US007575922B2

(12) United States Patent
Yamana et al.

(10) Patent No.: US 7,575,922 B2
(45) Date of Patent: Aug. 18, 2009

(54) POLYPEPTIDE AND GENE ENCODING THE SAME

(75) Inventors: Kei Yamana, Hino (JP); Yukimi Nagasawa, Hino (JP); Hitoshi Wada, Hino (JP); Yoshinori Kasahara, Hino (JP)

(73) Assignee: Teijin Limited, Osaka (JP)

( * ) Notice: Subject to any disclaimer, the term of this patent is extended or adjusted under 35 U.S.C. 154(b) by 229 days.

(21) Appl. No.: 11/196,618

(22) Filed: Aug. 4, 2005

(65) Prior Publication Data

US 2005/0272127 A1 Dec. 8, 2005

Related U.S. Application Data

(62) Division of application No. 11/055,967, filed on Feb. 14, 2005, which is a division of application No. 10/089,600, filed as application No. PCT/JP00/06804 on Sep. 29, 2000, now abandoned.

(30) Foreign Application Priority Data

Sep. 29, 1999 (JP) ................................. 11-275947

(51) Int. Cl.
*C12N 15/85* (2006.01)
(52) U.S. Cl. .................. 435/326; 530/387.1; 530/388.1; 530/388.8
(58) Field of Classification Search ................. 435/326; 530/387.1, 388.1, 388.7
See application file for complete search history.

(56) References Cited

U.S. PATENT DOCUMENTS

| 5,719,125 A | 2/1998 | Suzuki et al. |
| 2002/0119130 A1 | 8/2002 | Eaton et al. |
| 2003/0073129 A1 | 4/2003 | Baker et al. |

FOREIGN PATENT DOCUMENTS

| CA | 2481685 A1 | 3/2001 |
| EP | 0624645 A1 | 11/1994 |
| EP | 0 869 180 A1 | 10/1998 |
| WO | WO 00/12708 | 3/2000 |
| WO | WO 00/29579 | 5/2000 |
| WO | WO 00/43495 A | 7/2000 |
| WO | WO 00/78961 A | 12/2000 |
| WO | WO 01/16318 A | 3/2001 |
| WO | WO 01/22920 A | 4/2001 |
| WO | WO 01/40466 A | 6/2001 |
| WO | WO 01/48203 A | 7/2001 |
| WO | WO 01/53344 A | 7/2001 |

OTHER PUBLICATIONS

Stanton, P et al, 1994, Br J Cancer, 70: 427-433.*
Iehle, C et al, 1999, J Steroid Biochem Mol Biol, 68: 189-195.*
Abbaszadegan, M R, et al, 1994, Cancer Res, 54: 4676-4679.*
MSN Health News, 2000, pp. 1-5.*
Gura, 1997, (Science, 278:1041-1042).*
Jain, 1994 (Sci. Am., 271:58-65).*
Curti, 1993 (Crit. Rev. in Oncology/Hematology, 14:29-39).*
Kimmel et al, 1987 (J. Neurosurg, 66:161-171).*
Bowie (Science, 1990, 257 : 1306-1310).*
Roger, I et al, 1988, Bioscience Reports, 8(4): 359-368.*
MPSRCH search result, 2007, us-11-196-618.2.rapbm, result 2, pp. 1-2.*
Kyoko et al, 2008, Cancer science, 2008, 99(3): 459-66.*
Zips et al, 2005, In vivo, 19: 1-8.*
Lee et al, 1999, J Immunol, 163: 6292-6300.*
Kirkin et al, 1998, APMIS, 106 : 665-679.*
Bowie et al: "Deciphering the Message in Protein Sequences: Tolerance to Amino Acid Substitutions", Science, 1990, vol. 257, pp. 1306-1310.
Burgess et al; "Activity of Heparin-binding (Acidic Fibroblast) Growth Factor-1 from its Receptor-binding Activities by Site-directed Mutagenesis of a Single Lysine Residue", The Rockefeller University Press., Journal of Cell Biology, 1990, vol. 111, pp. 2129-2138.
Lazar et al: "Transforming Growth Factor α: Mutation of Aspartic Acid 47 and Leucine 48 Results in Different Biological Activities", Molecular and Cell Biology, 1988, vol. 8, No. 3, pp. 1247-1252.
Tao et al: "Role of Carbohydrate in the Structure and Effector Functions Mediated by the Human IgG Constant Region[1]", The Journal of Immunology, 1989, vol. 143, No. 8, pp. 2595-2601.
Gillies et al: "Antigen binding and biological activities of engineered mutant chimeric antibodies with human tumor specificities", Human Antibodies and Hybridomas, 1990, vol. 1, No. 1, pp. 47-54.
MSN Health News, 2000, pp. 1-5.
MPSRCH search report, 2004, us-10-089-600-2.rapb, pp. 1-3, 6-7.
Hiraki, Yuji, et al. "Molecular cloning of human chondromodulin-I, a cartilage-derived growth modulatng factor, and its express in Chinese hamster ovary cells", European Journal of Biochemistry, vol. 260, No. 3, Mar. 1999, pp. 869-878, XP002279021 ISSN: 0014-2956.
Database EBI 'Online! Sep. 14, 1999 Lawlor S.: Human DNA sequence from clone RP3-419J7 on chromosome Xq21.33-23. Contains part of a gene similar to chondromodulin-1. Database accession No. AL035608 XP002279022.
Database EBI 'Online! Est, Dec. 18, 1994 Liew C.C.: "A533F heart *Homo sapiens* cDNA clone A533 similar to chondromodulin, mRNA sequence." Database accession No. T12179 XP0022979023.
Database EBI 'Online! Est, Mar. 18, 1997 Adams M.D.: "EST112774 Embryo, 12 week *Homo sapiens* cDNA 5' end similar to chondromodulin 1." Database accession No. AA297231 XP002279024.

(Continued)

*Primary Examiner*—Larry R. Helms
*Assistant Examiner*—Minh-Tam Davis
(74) *Attorney, Agent, or Firm*—Sughrue Mion, PLLC

(57) ABSTRACT

A polypeptide having the amino acid sequence as set forth in SEQ ID NO: 2, 4, or 6, a DNA encoding the same, and an antibody against said polypeptide, and the use thereof. The above amino acid sequence has a homology with chondromodulin-I that has an effect of controlling the growth and differentiation of chondrocytes and inhibiting angiogenesis.

6 Claims, 10 Drawing Sheets

OTHER PUBLICATIONS

Database EBI 'Online! Est, Jul. 1, 1998 NCI-CGAP: "ox30b10.s1 Soares_total_fetus_Nb2HF8_9w *Homo sapiens* cDNA clone Image: 1657819 3' similar to SW:CHMI_BOVIN PI7404 chondromodulin-1, Mrna sequence." Database accession No. A1039039 XP002279025.

Databse EBI 'Online! Est, Mar. 29, 2000 NCI-CGAP: "ur24h02.y1 Soares_mouse_NMBP *Mus musculus* cDNA clone Image: 302529 similar to TR:q9yi63 Chondromodulin-1 Precursor, mRNA sequence" Database accession No. AW743952 XP002279026.

Database EBI 'Online! Est, Jul. 18, 1996 Marra M.: mf97el2.rl Soares mouse embryo NbME13.5 14.5 Mus musculus cDNA clone Image: 422254 5' similar to SW: CHM1_bovin p17404 chondromodulin-I, mRNA sequence Database accession No. W97621 XP002279027.

Database EBI 'Online! EST, Mar. 4, 2000 Lee N. H.: EST291897 Normalized rat embryo, Bento Soares Rattus sp. cDNA clone 5' end similar to chondromodulin-I, mRNA sequence Database accession No. AW144807 XP002279028.

Canadian Office Action issued in Application No. 2,386,141, dated Aug. 11, 2008.

* cited by examiner

Fig.1A hChM-I : human ChM-I
hChM1L : human ChM1L

```
hChM-I   MTENSDKVPIALVGPDDVEFCSPPAYATLTVKPSSPARLLKVGAVVLISGAVLLLFGAIG
hChM1L   ---------MAKNPPENCEDCHILNAEAFKSKK--ICKSLKICGLVFGILALTLIVLFWG
                  *   *  **         *        **   *    *    *      * hChM-I   AFYFWKGSDSHIYNVHYTMSINGKLQDGSMEIDAGNNLETFKMGSGAEEAIAVNDFQNGI
hChM1L   SKHFWPEVPKKAYDMEHTFYSNGEKKKIYMEIDPVTRTEIFRSGNGTDETLEVHDFKNGY
          * **        *    *         **      *   *  *    *   * hChM-I   TGIRFAGGEKCYIKAQVKARIPEVGAVTKQSISSKLEGKIMPVKYEENSLIWVAVDQPVK
hChM1L   TGIYFVGLQKCFIKTQIKV-IPEFSEPEEEID----ENEEITTTFFEQSVIWVPAEKPIE
         *** *     *  *   ***            *         * * ***       * hChM-I   DNSFLS-SKVLELCGDLPIFWLKPTYP--KEIQRERREVVRKIVPTTTKRPHSGPRSNPG
hChM1L   NRDFLKNSKILEICDNVTMYWINPTLISVSELQDFEEEGEDLHFPANEKKGIEQNEQWVV
          *        *   **  *    *  **        *        *    * hChM-I   AGRLNNETRPSVQEDSQAFNPDNPYHQQEGESMTFDPRLDHEGICCIECRRSYTHCQKIC
hChM1L   PQVKVEKTRHAR----QASEEELPINDYTENGIEFDPMLDERGYCCIYCRRGNRYCRRVC
               * *   **          * *         *   * * *       *  * hChM-I   EPLGGYYPWPYNYQGCRSACRVIMPCSWWVARILGMV
hChM1L   EPLLGYYPYPYCYQGGRVICRVIMPCNWWVARMLGRV
         *** **** ** *** *    ******* ***** ** *
```

Fig.1B hChM1L : human ChM1L
mChM1L : mouse ChM1L
rChM1L : rat ChM1L

```
mChM1L    MAKNPPENCEGCHILNAEALKSKKICKSLKICGLVFGILALTLIVLFWGSKHFWPEVSKK
rChM1L    MAKNPPENCEGCHILNAEALKSKKIRKSLKICGLVFGILALTLIVLFWGSKHFWPEVSKK
hChM1L    MAKNPPENCEDCHILNAEAFKSKKICKSLKICGLVFGILALTLIVLFWGSKHFWPEVPKK
          ******** *** * ********************** mChM1L    TYDMEHTFYSNGEKKKIYMEIDPITRTEIFRSGNGTDETLEVHDFKNGYTGIYFVGLQKC
rChM1L    TYGMEHTFYSNGEKKKISMEIDPITRTEIFRSGNGTDETLEVHDFKNGYTGIYFVGLQKC
hChM1L    AYDMEHTFYSNGEKKKIYMEIDPVTRTEIFRSGNGTDETLEVHDFKNGYTGIYFVGLQKC
            *********** * ************************************** mChM1L    FIKTQIKVIPEFSEPEEEIDENEEITTTFFEQSVIWVPAEKPIENRDFLKNSKILEICDN
rChM1L    FIKTQIKVIPEFSEPEEEIDENEEITTTFFEQSVIWVPAEKPIENRDFLKNSKILEICDN
hChM1L    FIKTQIKVIPEFSEPEEEIDENEEITTTFFEQSVIWVPAEKPIENRDFLKNSKILEICDN
          ************************************************************ mChM1L    VTMYWINPTLIAVSELQDFEEDGEDLHFPTSEKKGIDQNEQWVVPQVKVEKTRHTRQASE
rChM1L    VTMYWINPTLIAVSELQDFEEDGEDLHFPTSEKKGIDQNEQWVVPQVKVEKTRRTRQASE
hChM1L    VTMYWINPTLISVSELQDFEEEGEDLHFPANEKKGIEQNEQWVVPQVKVEKTRHARQASE
          ********* ***** *** ** *********** ** mChM1L    EDLPINDYTENGIEFDPMLDERGYCCIYCRRGNRYCRRVCEPLLGYYPYPYCYQGGRVIC
rChM1L    EDLPVNDYTENGIEFDPMLDERGYCCIYCRRGNRYCRRVCEPLLGYYPYPYCYQGGRVIC
hChM1L    EELPINDYTENGIEFDPMLDERGYCCIYCRRGNRYCRRVCEPLLGYYPYPYCYQGGRVIC
          *  **************************************************** mChM1L    RVIMPCNWWVARMLGRV
rChM1L    RVIMPCNWWVARMLGRV
hChM1L    RVIMPCNWWVARMLGRV
          *****************
```

Fig. 2
(a) hChM-I : human ChM-I
(b) hChM1L : human ChM1L
(c) mChM1L : mouse ChM1L
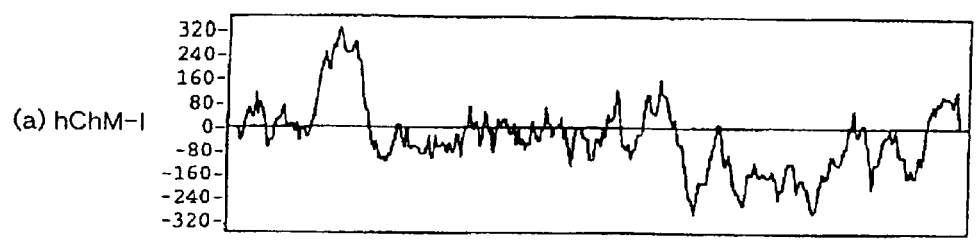
(a) hChM-I
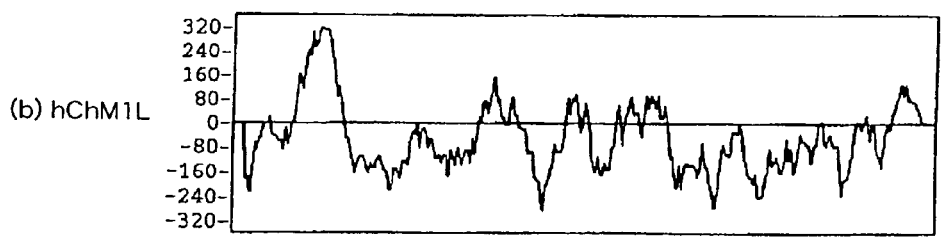
(b) hChM1L
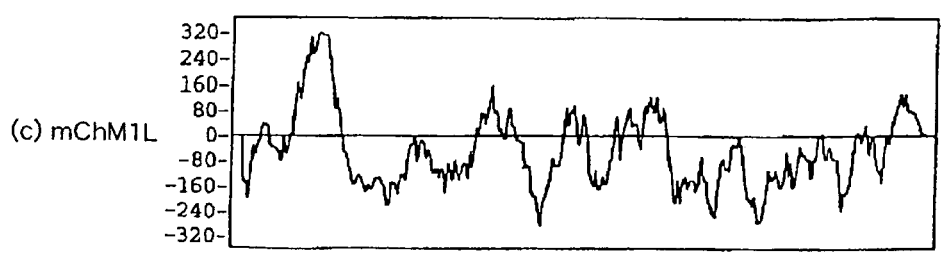
(c) mChM1L

Fig. 3

(a) EXPRESSION AT VARIOUS TISSUES OF ADULT (10-WEEK OLD)
1. BRAIN, 2. EYEBALL, 3. LUNG, 4. THYMUS, 5. HEART, 6. LIVER, 7. KIDNEY, 8. STOMACH, 9. SPLEEN, 10. SKELETAL MUSCLE, 11. WHOLE RIB, 12. FAT, 13. ADRENAL, 14. PITUITARY, 15. THYROID, 16. INTESTINE (b) EXPRESSION AT VARIOUS TISSUES OF FETUS (DAY 17 OF GESTATION)
1. BRAIN, 2. EYEBALL, 3. LUNG, 4. THYMUS, 5. HEART, 6. LIVER, 7. KIDNEY, 8. SPLEEN, 9. STOMACH, 10. INTESTINE, 11. WHOLE RIB, 12. TRACHEA, 13. PANCREAS (c) EXPRESSION DURING THE DEVELOPMENTAL STAGE OF FETUS
1. DAY 10 OF GESTATION, 2. DAY 11 OF GESTATION, 3. DAY 12 OF GESTATION, 4. DAY 13 OF GESTATION, 5. DAY 14 OF GESTATION, 6. DAY 15 OF GESTATION, 7. DAY 16 OF GESTATION, 8. DAY 17 OF GESTATION, 9. DAY 18 OF GESTATION, 10. DAY OF CHILDBIRTH (a)

(b)
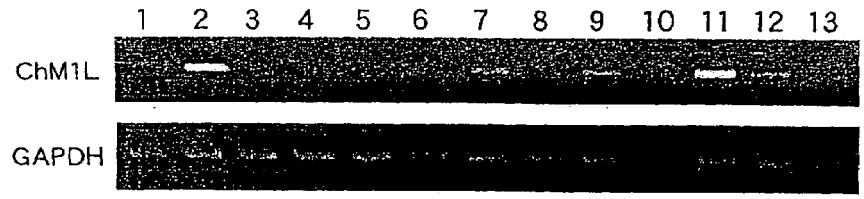

(c)
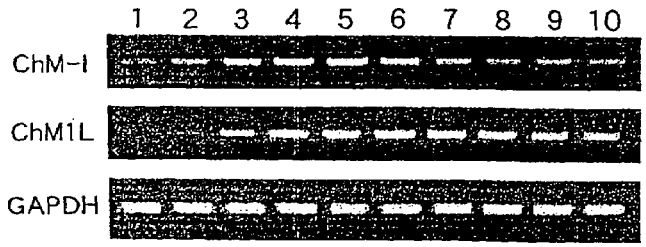

(a) SDS-PAGE: 1. MOCK, 2. HUMAN ChM1L, 3. MOUSE ChM1L
(b) SDS-PAGE: 1. MOCK, 2. HUMAN ChM1L(His), 3. MOUSE ChM1L(His)
(c) WESTERN BLOT (DETECTION WITH ANTI-PEPTIDE ANTIBODY):
    1. MOCK, 2. HUMAN ChM1L, 3. MOUSE ChM1L
(d) WESTERN BLOT (DETECTION WITH ANTI-His TAG ANTIBODY):
    1. MOCK, 2. HUMAN ChM1L(His), 3. MOUSE ChM1L(His)

1. Mock
2. soluble human ChM1L

1. NON-TREATED, 2. TREATED WITH NANase II + O-GLYCOSIDASE DS + PNGase F, 3. TREATED WITH NANase II, 4. TREATED WITH O-GLYCOSIDASE DS, AND 5. TREATED WITH PNGase F

Fig.7
(a) RABBIT IgG
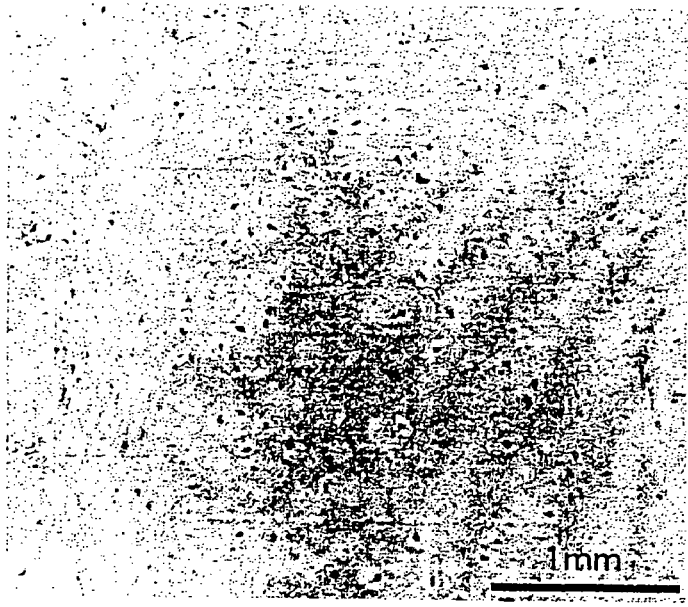
(b) ANTI-ChM1L PEPTIDE ANTIBODY
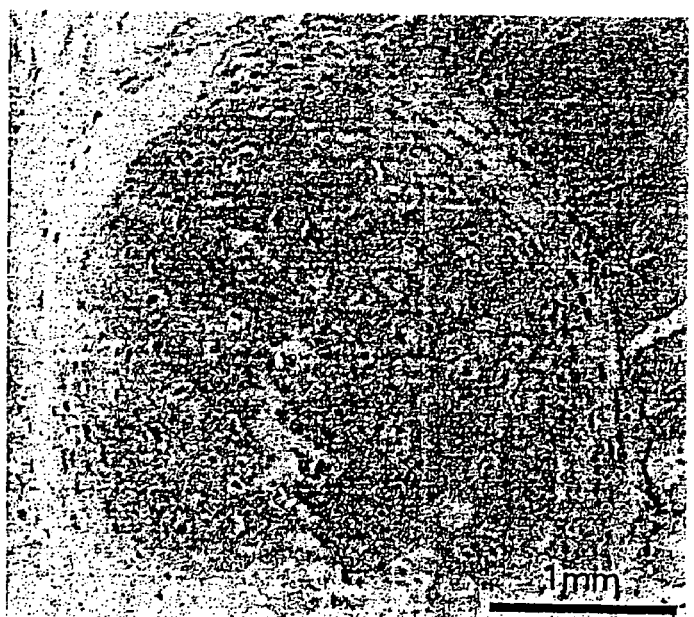

Fig. 9
(a) Buffer control
(b) BSA (20ug/well)
(c) shChM1L (10ug/well)
(d) shChM1L (20ug/well)
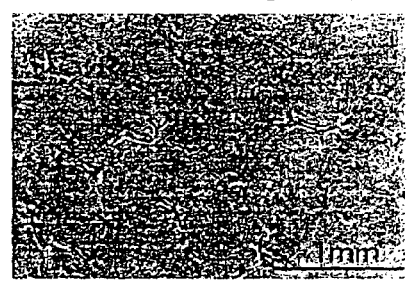
(e) PF-4 (1ug/well)
(f) PF-4 (10ug/well)
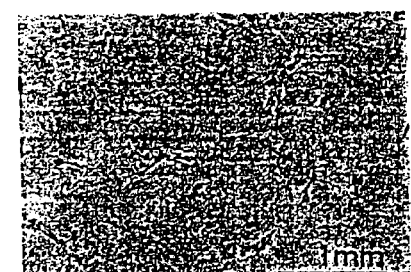

POLYPEPTIDE AND GENE ENCODING THE SAME

This is a divisional of U.S. Ser. No. 11/055,967 filed Feb. 14, 2005, which is a divisional of U.S. Ser. No. 10/089,600 filed Mar. 29, 2002, now abandoned, which is a National Stage application filed under 35 U.S.C. § 371 of PCT/JP00/06804 filed Sep. 29, 2000.

FIELD OF THE INVENTION

The present invention relates to a novel human, mouse and rat polypeptide having a homology in the amino acid sequence with chondromodulin-I (ChM-I) that is known to have an effect of controlling the growth and differentiation of chondrocytes and inhibiting angiogenesis, and a human, mouse and rat gene (hereinafter referred to as "ChM1L gene") encoding the same.

BACKGROUND ART

Almost all the bones of mammals are formed through a mechanism called "endochondral bone formation" in which chondrocytes calcify via the growth and differentiation thereof, and are finally replaced with bone. It is known that a variety of hormones and growth factors participate in this series of process, including insulin-like growth factor (IGF1, IGF2), fibroblast growth factor (FGF), transforming growth factor (TGF), growth hormone and the like. Hiraki et al. isolated ChM-I gene as a factor, in addition to the above hormones and growth factors, that facilitates the growth and differentiation of chondrocytes (Biochem. Biophys. Res. Commun., 175, 971-977, 1991, European Patent Publication No. 473080). Human ChM-I is synthesized as a type II membrane protein comprising 334 amino acid residues and, after glycosylation, undergoes processing with a result that the C-terminal portion comprising 120 amino acid residues are extracellularly secreted (Hiraki et al., Eur. J. Biochem. 260, 869-878, 1999). ChM-I not only promotes the growth of cultured chondrocytes but potently promotes proteoglycan synthesis and the colony formation of chondrocytes in agarose (Inoue et al., Biochem. Biophys. Res. Commun., 241, 395-400, 1997). ChM-I also promotes the growth of osteoblasts (Mori et al., FEBS Letters, 406, 310-314, 1997).

On the other hand, it has long been pointed out that cartilage remains not only avascular but resistant to infiltration of blood vessels. Hiraki et al. attempted to purify a growth inhibiting factor for vascular endothelial cells from the extracts of cartilaginous tissue, and have succeeded in the complete purification thereof. As a result, it was found to be ChM-I (Hiraki et al., FEBS Letters, 415, 321-324, 1997; Hiraki et al., J. Biol. Chem., 272, 32419-32426, 1997). Generally, the cartilaginous tissue is characterized by being avascular, but in the replacement to the bone tissue, it is believed, infiltration of blood vessels into the cartilaginous tissue is required. In the scheduled region of vascular invasion, the hypertrophy of cartilaginous tissue and the calcification of cartilage matrix occur prior to vascular invasion to be ready for forming the primary point of ossification. In the region where the hypertrophic cartilage and the subsequent ossified cartilage appear, the expression of ChM-I dramatically decreases. Thus, although the expression of the ChM-I gene is cartilage-specific, it is limited to the avascular cartilage that is resistant to vascular invasion. As described above, it is believed that ChM-I not only promotes the growth, differentiation, and maturing of cartilage but inhibits the infiltration of blood vessels by inhibiting the growth of vascular endothelial cells. Thus, the expression in the avascular cartilage and the disappearance of expression in the ossified layer prior to vascular invasion are in good agreement with the bifunctional effect of ChM-I.

In the cartilaginous tissue, bFGF that is a potent angiogenic factor is accumulated in pericellular space in large quantities, and it has been elucidated that ChM-I is present in interterritorial space in such a way as to surround bFGF (Hiraki et al., J. Biol. Chem., 272, 32419-32426, 1997). Thus, in the avascular cartilage, ChM-I is present in a form that masks the angiogenic factor, and it is thought that the angiogenenic effect of ChM-I may account for the absence of blood vessels in the cartilage (Tanpakusitsu kagaku koso, Vol. 40, No. 5, 1995). It has also been confirmed that ChM-I suppresses the growth of tumor cells by inhibiting the infiltration of blood vessels into human tumor cells in vivo (Hayami et al., FEBS Letters, 458, 436-440, 1999). The expression analysis of ChM-I in various mouse tissues revealed that ChM-I is expressed in the eye and the thymus in addition to the cartilage, but the function of ChM-I in these tissues has yet to be elucidated (Shukunami et al., Int. J. Dev. Biol. 43, 39-49, 1999).

The growth and the expression of differentiation function of chondrocytes plays an important role in the healing process from fracture or various cartilage diseases. Thus ChM-I, a factor that promotes the growth and differentiation of chondrocytes, is a promising candidate for an agent that promotes the growth of chondrocytes (Kokai (Japanese Unexamined Patent Publication) No. 7-138295). In the growth or metastasis of tumor cells, infiltration of blood vessels into tissues is required to obtain energy necessary therefore. Therefore ChM-I that has an effect of inhibiting angiogenesis is also a likely candidate for an anti-cancer agent (Kokai (Japanese Unexamined Patent Publication) No. 7-138295). As described above, ChM-I not only controls the growth and differentiation of chondrocytes but inhibits angiogenesis, and hence its application into drugs is being awaited.

In recent years, biotechnology has made rapid progress, and in association with the development of the human genome project as well, a great number of new genes are being cloned. It is said that the number of human genes amounts to about 100,000, and among the genes groups of molecules having a homology in the amino acid sequences sometimes form families. As the groups of molecules having a homology in the amino acid sequences, various gene families are known such as the TNF family, the TNF receptor family, the chemokine family, G-protein coupled receptor family and many other gene families. For example, as the molecules belonging to the TNF family, there are known about 20 molecules including tumor necrosis factor α (TNFα, Pennica et al., Nature 312, 724, 1984), Fas ligand (FasL, Suda et al., Cell 75, 1167, 1993), TNF-related apoptosis-inducing ligand (TRAIL, Steven et al., Immunity 3, 673, 1995), B lymphocyte stimulator (BLYS, Moore et al., Science 285, 260-263, 1999), and the like.

The molecules belonging to the TNF family are type II membrane proteins and have a homology in the amino acid sequence in the extracellular region. Although homology in the amino acid sequence is noted, these molecules have been demonstrated to have their inherent functions, and their application as pharmaceutical agents have been attempted in a variety of diseases. It has also been shown that the molecules of the TNF family have their unique receptors, and the application thereof as pharmaceutical agents have also been attempted. In fact, some have been approved as pharmaceutical products (for example, soluble TNF receptor, by Immunex). Research and development is also in progress on antibodies against these molecules as pharmaceutical drugs, and in fact, some have been approved as pharmaceutical products (for example, anti-TNF-α antibody, by Centocore). As examples of molecules having a homology in the amino acid sequence that were applied into the development of pharmaceutical products, the TNF family and the TNF receptor family were illustrated as above. Some of the underlying reasons that enabled the application of these molecules into pharmaceutical products are the facts that the functions of each of these molecules were analyzed and the similarity and the difference between them were elucidated.

Molecules of the TNF family have the structure of type II membrane proteins and since many of them are expressed mostly in the blood system and the lymphatic system, they have a lot in common in terms of experimental techniques and samples. It is therefore expected that when a new gene belonging to the TNF family was discovered, the speed at which its function was analyzed must have been faster than the molecules discovered earlier. Thus, the discovery of a novel gene having a homology in the amino acid sequence and the analysis of its function would not only facilitates the functional analysis of novel genes to be discovered in the future but the result of analysis permits its comparison with the existing molecules, and therefore it is expected that more detailed findings on the functions of the existing molecules could be obtained.

Generally, when a novel gene encoding a protein having a homology in the amino acid sequence with existing molecules is cloned, the techniques and materials to be used for functional analysis may be referred to the examples of the existing molecules. However, even a molecule having a homology in the amino acid sequence is thought to have its own unique function as in the above-mentioned TNF family, and thus when its application into pharmaceutical products is envisaged, it is necessary to demonstrate the expression and purification of the recombinant protein, the generation of antibody, the expression of mRNA and protein at various tissues and the like, and thereby to clarify the difference in the structure and function from the existing molecules.

DISCLOSURE OF THE INVENTION

Thus, it is an object of the present invention to provide a new polypeptide similar to ChM-I and a gene encoding the same. It is also an object of the present invention to implement the generation of antibody against said polypeptide, the analysis of expression levels of said gene and the polypeptide, the expression and structural analysis of the recombinant protein and the like in order to clarify its similarity and difference with ChM-I, and to elucidate the function so as to enable the elucidation of pathological states, diagnosis, treatment etc. of diseases in which they are involved.

ChM-I is a type II membrane protein that regulates the growth and differentiation of chondrocytes and inhibits angiogenesis, and is a promising candidate for application into pharmaceutical products. Thus, once a gene encoding a new polypeptide similar to ChM-I has been provided, it is believed, its expression level in various cells and its structure and function can be analyzed, and the analysis of the expression products would enable the elucidation of pathology, diagnosis and treatment etc. of diseases in which they are involved. At present, however, there are no reports on molecules having a homology with the amino acid sequence of ChM-I, and it is unknown whether ChM-I forms a gene family or not. Thus, if a new polypeptide similar to ChM-I and a gene encoding the same are shown to be present, the analysis of structure, function etc. thereof would permit the study on its similarity and difference with ChM-I, which in turn would accelerates the elucidation of physiological functions of the molecules with one another, the elucidation of pathological states in which these molecules are involved, diagnosis, the development of therapeutic agents and the like.

After intensive and extensive research to attain the above purposes, the inventors of the present invention have succeeded in isolating a gene (ChM1L gene) that meets the above purposes, from human, mouse and rat cDNA libraries, and carried out the analysis of its expression level in various tissues, the generation of an antibody against said polypeptide, the expression of a polypeptide encoded by said gene in a mammalian cell, its detection and purification and the like, demonstrating that said polypeptide has an effect of inhibiting angiogenesis, and we hereby have completed the present invention.

Thus, the present invention is a gene encoding a polypeptide that substantially comprises the amino acid sequence as set forth in SEQ ID NO: 2, 4, and 6. As the above gene, there can be mentioned the nucleotide sequence represented by SEQ ID NO: 1, 3, and 5.

Furthermore, the present invention is a polypeptide encoded by a human, mouse and rat gene which polypeptide substantially comprises the amino acid sequence as set forth in SEQ ID NO: 2, 4 and 6.

The present invention is also an oligonucleotide probe that hybridizes to at least part of the above gene.

The present invention is also a recombinant DNA comprising the above gene.

The present invention is also a transformant transformed with the above recombinant DNA.

The present invention is also a method of producing the above polypeptide which method comprises culturing the above transformant and harvesting a polypeptide encoded by the gene of the present invention from the culture.

The present invention is also a monoclonal antibody or polyclonal antibody that specifically reacts with the above polypeptide.

The present invention is also a hybridoma that produces the above monoclonal antibody that is obtained by fusing an antibody-producing cell immunized with the above polypeptide to a myeloma cell.

The present invention is also a reagent for detecting genes said reagent comprising the above oligonucleotide probe.

The present invention is also a diagnostic kit that comprises the above polypeptide and the above monoclonal antibody or polyclonal antibody.

The present invention is also a pharmaceutical composition comprising a polypeptide encoded by the gene that substantially comprises the amino acid sequence as set forth in SEQ ID NO: 2, 4, or 6.

The present invention is also a pharmaceutical composition comprising a monoclonal antibody or a polyclonal antibody that specifically reacts with the above polypeptide.

The present invention is also a pharmaceutical composition comprising an antisense oligonucleotide that specifically hybridizes to part of the above gene.

The present invention is also a pharmaceutical composition comprising a nucleic acid that can be used in gene therapy said composition comprising at least part of the above gene.

The present invention is also a polypeptide wherein the above polypeptide is a membrane-bound form.

The present invention is also a gene encoding the above membrane-bound polypeptide.

The present invention is also a gene wherein the above human gene is present on chromosome X.

The present invention is also a polypeptide wherein the above polypeptide has an effect of inhibiting angiogenesis.

The present invention is also a gene encoding the above polypeptide that has the above effect of inhibiting angiogenesis.

BRIEF EXPLANATION OF THE DRAWINGS

FIG. 1A is a result in which the homology of amino acid sequences of human ChM1L and human ChM-I were compared.

FIG. 1B is a result in which the homology of amino acid sequences of human, mouse and rat ChM1L were compared.

FIG. 2 shows a hydrophobic profile of the amino acid sequences of human ChM-I, human ChM1L, and mouse ChM1L.

FIG. 3 shows the result of expression analysis of ChM1L mRNA in various tissues of adult and fetal mice, and the expression analysis of ChM1L and ChM-I mRNA in the developmental stage of a fetal mouse.

FIG. 7 shows the result in which the expression of ChM1L protein in mouse rib cartilage was detected by immunostaining using anti-ChM1L polypeptide antibody.

FIG. 9 shows the result in which the tube-like structure-forming system of the human umbilical vein endothelial cells were treated with (a) the buffer alone, (b) 20 µg of bovine serum albumin (BSA), (c) 10 µg of soluble human ChM1L, (d) 20 µg of soluble human ChM1L, (e) 1 µg of platelet factor 4 (PF-4), and (f) 10 µg of PF-4.

BEST MODE FOR CARRYING OUT THE INVENTION

In accordance with the present invention, "substantially comprise" means that the gene or polypeptide of the present invention, as long as it retains its function, may have mutations such as substitution, insertion, or deletion in the nucleotide sequence as set forth in SEQ ID NO: 1, 3, or 5 or the amino acid sequence as set forth in SEQ ID NO: 2, 4, or 6.

The ChM1L gene sequence of the present invention may be obtained by the RACE method (RACE: Rapid amplification of cDNA ends; Frohman, M. A. et al., Proc. Natl. Acad. Sci. USA, 85, 8998-9002, 1988), the outline of which method is as follows:

Generally, the RACE method enables one to obtain a full-length cDNA in an efficient manner, when a portion of a cDNA sequence is known. Primers are constructed from known sequence regions to permit elongation in each of the 3'-end or 5'-end direction, and then cDNA is amplified by the polymerase chain reaction (PCR, Science, 230, 1350-1354, 1985). When a PCR method is carried out, primers that specifically anneal are used in the known region, and primers that anneal to the sequence tagged by a ligation reaction are used in the 3'-end and the 5'-end. Thus, the regions amplified by PCR contain unknown regions. The isolation and purification of the amplified cDNA fragment can be performed according to a standard method as described below, for example gel electrophoresis may be employed. The determination of nucleotide sequence of the DNA fragment thus obtained may be performed according to a standard method such as the dideoxy method (Proc. Natl. Acad. Sci. USA, 74, 5463-5467, 1977) and the Maxam-Gilbert method (Methods in Enzymology, 65, 499, 1980). Such determination of nucleotide sequences may also be carried out using commercially available sequencing kits, etc.

More specifically, it is outlined as follows, though more detailed explanations thereof will be made hereinafter in Example 2. Using the amino acid sequence of human ChM-I, TBLASTN search was performed for the EST data base (dbEST, EST: Expressed sequence tag) in the DNA data bank of Japan (DDBJ) to detect an EST file, GenbanK accession number AI123839. AI123839, which is a nucleotide sequence fragment registered in dbEST, was found for the first time by the above TBLASTN search to be a novel gene fragment encoding an amino acid sequence similar to ChM-I. Thus, primers were synthesized from part of the sequence of cDNA obtained from dbEST, and the sequence of human ChM1L gene was determined using the RACE method. Subsequently, the sequences of mouse and rat ChM1L genes were similarly determined. The sequences of human, mouse and rat ChM1L genes are shown in SEQ ID NO: 1, 3 and 5, and the amino acid sequences of the peptides encoded thereby are shown in SEQ ID NO: 2, 4 and 6.

Figure 4:
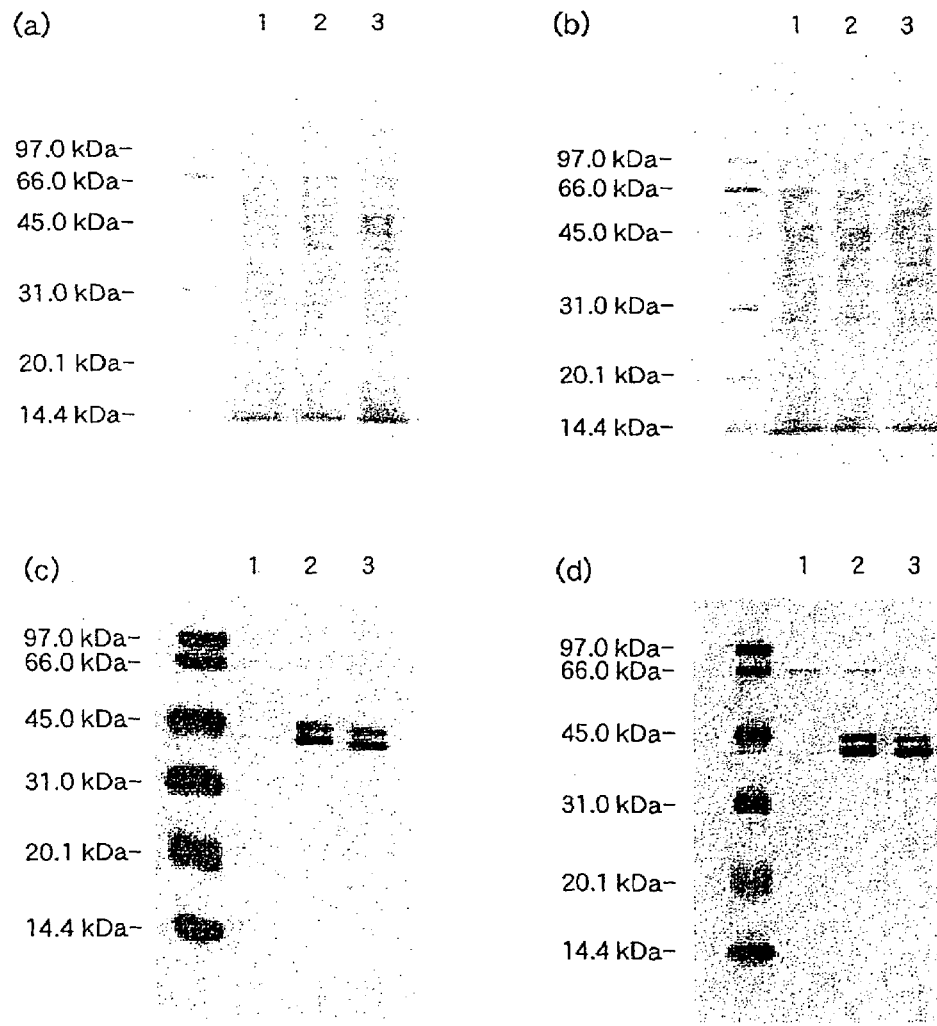
FIG. 4 shows a result in which human and mouse ChM1L proteins were expressed in COS7 cells and detected by Western blot. (a) shows the result in which Mock (lane 1), human ChM1L (lane 2), and mouse ChM1L (lane 3) were transfected, and the cellular components were subjected to electrophoresis and stained with Coomassie brilliant blue; (c) shows the result in which the same samples as above were detected by Western blot using anti-ChM1L peptide antibody; (b) shows the result in which Mock (lane 1), human ChM1L (His-tagged) (lane 2), and mouse ChM1L (His-tagged) (lane 3) were transfected, and the cellular components were electrophoresed and stained with Coomassie brilliant blue; (d) shows the result in which the same samples as above were detected by Western blot using anti-His tag antibody.

The polypeptides encoded by the ChM1L genes of the present invention are composed of 317 amino acids (SEQ ID NO: 2, 4 and 6). The amino acid sequence of ChM1L has a homology with ChM-I, in particular a very high homology with the C-terminal portion that is extracellularly secreted after the processing of ChM-I (FIG. 1(a)). The amino acid sequences of ChM1L have a very high homology in between humans, mice, and rats (FIG. 1(b)). From the hydrophobicity analysis of the amino acid sequence, ChM1L similarly to ChM-I is thought to be a molecule having the structure of the type II membrane proteins (FIG. 2). As shown in FIG. 2, in both of said polypeptide and ChM-I, a hydrophobic domain comprising about 20 amino acids that is uniquely found in molecules having a membrane-binding activity is present in the vicinity of several dozen amino acids from the N-terminal. That said polypeptide is a molecule having the type II membrane protein structure was also demonstrated by the result in Example 8 in which said polypeptide was expressed in COS7 cells (FIG. 4).

The human ChM1L gene of the present invention was shown, as described below in Example 12, to be present on chromosome X (GenbanK accession No. AL035608).

As the ChM1L gene of the present invention, there can be mentioned cDNA, chemically synthesized DNA, DNA isolated by PCR, genomic DNA and combinations thereof. Using a standard method, said genomic DNA may also be isolated by hybridization with the ChM1L gene that is disclosed herein. RNA that was transcribed from said ChM1L gene is also encompassed in the present invention. The sequences of the gene of the present invention represented by SEQ ID NO: 1, 3 and 5 are a combination example of codons representing amino acid residues encoded by them. The ChM1L gene of the present invention is not limited to this, and it is also possible to have a DNA sequence obtained by combining codons to amino acid residues and then selected. The selection of said codon may be performed according to a standard method, and for example the frequency of use of host's codons to be used is taken into account (Nucleic Acids Research, 9, 43-74, 1981).

Furthermore, the ChM1L gene of the present invention encompasses DNA sequences encoding mutants in which parts of the amino acid sequence as set forth in SEQ ID NO: 2, 4, and 6 are substituted, deleted, or added. The production, modification (mutation) and the like of these polypeptides may naturally occur, and can be obtained by post-translational modification or by a genetic engineering method such as site-specific mutagenesis (Methods in Enzymology, 154, 350, 367-382, 1987; ibid., 100, 468, 1983; Nucleic Acids Research, 12, 9441, 1984; Zoku Seikagaku Jikken Koza 1 (Sequel to Biochemistry Experimental Series 1) "Idensi Kenkyuuhou II (Gene Study Method II)", edited by The Japanese Biochemical Society, 105, 1986) and the like.

The production of the ChM1L gene of the present invention may be readily performed by a common genetic engineering method based on the sequence information of the ChM1L gene of the present invention (Molecular Cloning, 2nd Ed., Cold Spring Harbor Laboratory Press, 1989; Zoku Seikagaku Jikken Koza (Sequel to Biochemistry Experimental Series) "Idensi Kenkyuuhou I, II, III (Gene Study Method I, II, III)", edited by The Japanese Biochemical Society, 1986).

This can be attained by, for example, selecting the desired clones from a cDNA library (prepared from a suitable cell source that expresses the ChM1L gene according to a standard method) using suitable probes and antibodies unique to the gene of the present invention (Proc. Natl. Acad. Sci. USA, 78, 6613, 1981; Science, 222, 778, 1983, and the like).

In the above method, as the cell source, there can be illustrated various cells, tissues, and cultured cells derived therefrom and the like that express the ChM1L gene, from which any of separation of total RNA, separation and purification of mRNA, and conversion (synthesis) into cDNA, cloning etc. may be performed according to a standard method. cDNA libraries are commercially available, and in the present invention, these cDNA libraries such as various cDNA libraries commercially available from Clontech can be used.

The screening of the ChM1L gene of the present invention from a cDNA library may be carried out according to the above standard method. As the above screening method for, for example a polypeptide produced by cDNA, there can be illustrated a method of selecting a corresponding cDNA clone by immunological screening using a specific antibody against a polypeptide encoded by the ChM1L gene of the present invention, a plaque hybridization method using a probe that selectively binds to the nucleotide sequence of interest, a colony hybridization method and the like as well as combinations thereof. Probes that may be used herein include a DNA sequence that was chemically synthesized based on the information on the DNA sequence of the ChM1L gene of the present invention, the ChM1L gene of the present invention that was already obtained and fragments thereof.

In order to obtain the ChM1L gene of the present invention, a PCR method for amplifying DNA/RNA can be preferably used. Primes for use in such a method can be appropriately selected based on the sequence information of the ChM1L gene of the present invention that was elucidated for the first time by the present invention, and can be synthesized according to a standard method.

More specifically, it is outlined as follows, though more detailed explanations thereof will be made hereinafter in Example 2. A primer is synthesized so as to contain the coding sequence of the ChM1L gene, and the it is used to amplify the ChM1L gene using a PCR method. Then, it is electrophoresed and the band of interest is excised, from which DNA is purified. The purified DNA and the plasmid vector are ligated and transformed into Escherichia coli (E. coli). Subsequently, the plasmid is purified from the E. coli culture liquid and the integration of the sequence of interest is confirmed using a DNA sequencer. The ChM1L gene thus cloned can be transferred to other plasmid vectors or virus vectors using suitable restriction enzymes.

Using the ChM1L gene (cDNA and genomic DNA) thus obtained, it is possible to create a genetically modified animal in which the expression of the ChM1L gene is increased, decreased, or lost by a standard method.

Based on the sequence information of the ChM1L gene of the present invention, the expression of the ChM1L gene of the present invention in various tissues can be detected using part or all of the nucleotide sequence of said gene. This can be advantageously accomplished according to standard methods such as the RT-PCR (reverse transcribed-polymerase chain reaction) (Kawasaki, E. S., et al., Amplification of RNA. In PCR Protocol, A Guide to methods and applications, Academic Press, Inc., SanDiego, 21-27, 1989) method, Northern blotting analysis (Molecular Cloning, Cold Spring Harbor Laboratory, 1989) and the like. Primers for the RT-PCR method and probes for Northern blotting analysis are not limited, as long as they are the sequences capable of specifically detecting the ChM1L gene, and such sequences can be appropriately determined based on the nucleotide sequence of the ChM1L gene of the present invention. Thus, the present invention provides primers and/or probes useful for the detection of the ChM1L gene. The above probes may also be used for the detection of genomic DNA by Southern blotting analysis.

As means to detect the expression of ChM1L mRNA, there can be illustrated the RT-PCR method described in Example 6. It is outlined as follows, though more detailed explanations thereof will be made hereinafter in Example 6.

After extracting each tissue and extracting RNA therefrom, it is subjected to a reverse transcription reaction to synthesize cDNA. Using this cDNA as a template, a PCR reaction is carried out, and the reaction mixture obtained is subjected to electrophoresis on agarose gel. Examining the band under UV irradiation, the amount of the ChM1L gene expressed in each tissue was detected. As a result, the expression of ChM1L mRNA in each tissue of an adult mouse was observed in the brain, the eyeball, the skeletal muscle, the whole rib and the thyroid (FIG. 3(a)). On the other hand, the expression of ChM-I mRNA in the mouse has been confirmed in the eyeball, the thymus, the cartilage and the whole rib (Shukunami et al., J. Dev. Biol. 43, 39-49, 1999). Thus, it was revealed that ChM1L and ChM-I are expressed at different tissues in the living body, and thus their physiological functions were considered to be different. The expression of ChM1L was observed, even at tissues such as the brain, the skeletal muscle, and the thyroid in which no expression of ChM-I has been confirmed.

Since ChM1L is also expressed in the eyeball that is a tissue in which ChM-I expression has been observed and that is resistant to vascular invasion and the whole rib containing cartilage, ChM1L is thought to be involved in angiogenesis. These results suggest that ChM1L may be associated with brain-related diseases such as Alzheimer's disease, skeletal muscle-related diseases such as muscular dystrophy, thyroid-related diseases such as Basedow's disease, eyeball-related diseases such as diabetic retinopathy, cartilaginous tissue-related diseases such as osteoarthritis and rheumatoid arthritis, and angiogenesis-related diseases such as cancer. Thus, the ChM1L gene and the ChM1L polypeptide of the present invention, antagonists and agonists to ChM1L including antibody that binds to ChM1L, agents that promote or reduce the expression of the ChM1L gene, and the like are considered to be used as therapeutic agents for these diseases. The agonists and antagonists mentioned above are intended to include peptides, proteins, low molecular weight compounds and the like, but the physical properties are not limited to them as long as they retain the function.

In various tissues of a fetus, the expression of ChM1L mRNA was noted in the eyeball, the kidney, the stomach, the whole rib and the trachea (FIG. 3(b)). In an adult mouse, ChM1L mRNA was not expressed in the kidney or the stomach, but the ChM1L mRNA was expressed in these tissues of the fetus suggests that ChM1L is involved in the development and morphogenesis of these organs. Thus, ChM1L is thought to be also associated with the repair and regeneration of these organs in adults. It was also revealed that ChM1L mRNA is expressed in the trachea. Thus, the ChM1L gene and the ChM1L polypeptide of the present invention, antagonists and agonists to ChM1L including antibody that binds to ChM1L, agents that promote or reduce the expression of the ChM1L gene, and the like are considered to be used as therapeutic agents for kidney-related diseases such as chronic kidney failure, stomach-related diseases such as gastric cancer and gastric ulcer, and trachea-related respiratory diseases such as chronic bronchitis and asthma.

In the developmental stage of the fetus, the expression of ChM1L mRNA is very weak at day 10 of gestation, and the expression increases at around days 11 to 13 (FIG. 3(c)). On the other hand, though ChM-I, similarly to ChM1L, increases in expression with the development of the fetus, it was evidently expressed more strongly than ChM1L on days 10 and 11 of gestation. It is, therefore, clear that ChM1L lags behind ChM-I in the expression, and that these molecules have different functions in the development of the fetus. The increase in ChM1L expression in the developmental stage of the fetus suggests that ChM1L is deeply involved in the generation of organs and the skeleton. Thus, the ChM1L gene and the ChM1L polypeptide of the present invention, antagonists and agonists to ChM1L including antibody that binds to ChM1L, agents that promote or reduce the expression of the ChM1L gene, and the like are considered to be used as agents for regenerating and repairing organs in the case of congenital diseases associated with inadequate development of the organs or acquired damages to the organs. Furthermore, since there are differences between ChM1L and ChM-I in the expression in various tissues in the adult and the fetus, and in the expression during the developmental stage of the fetus, it is expected that these molecules and drugs that target these molecules, when used as therapeutic agents, have different uses.

Using the sequence of the ChM1L gene of the present invention, it is possible to produce a polypeptide encoded by said gene by a gene engineering method.

The production of the above polypeptide may be performed by constructing a recombinant DNA that permits the expression of the ChM1L gene of the present invention in a host cell, introducing this into a host cell to transform it and then cultivating said transformant.

As the host cell, any of eukaryotic cells and prokaryotic cells can be used.

As the above eukaryotic cells, there may be mentioned vertebrates, yeasts, insect cells, and the like. As the vertebrate cells, there may be mentioned CHO cells, COS cells, and the like.

As the expression vector for vertebrates, there can be used those that have a promoter generally located upstream of the gene to be expressed, a polyadenylation site, a transcription termination sequence, and the like. As the above expression vector, for example there can be illustrated pSV2dhfr (Mol. Cell. Biol., 854, 1981), pcDNA3.1(+) (Invitrogen) and pCAGGS (Gene, 108, 193-200, 1991) that have the SV40 early promoter.

As means to express the polypeptide of interest in a eukaryotic cell, there are many systems known per se in the field of art.

For example, as a system that allows expression in yeasts, there can be mentioned "Expression of polypeptides in yeast" described in Kokai (Japanese Unexamined Patent Publication) No. 57-159489, as a system that allows expression in insect cells, there can be mentioned "Process for producing a recombinant baculovirus expression vector" described in Kokai (Japanese Unexamined Patent Publication) No. 60-37988, and as a system that allows expression in mammalian cells, there can be mentioned "Improvement of eukaryotic expression" described in Kokai (Japanese Unexamined Patent Publication) No. 2-171198, and there are many others.

The ChM1L gene of the present invention can also be expressed in prokaryotic host cells such as *E. coli, Bacillus subtilis*, and *Streptomyces*. For *E. coli* as above host cell, *Escherichia coli* strain K12 is often used, and as the vector pBR322 and improved vectors thereof are often used, but they are not limiting and many other known microbial stains and vectors may be used. As the promoter, for example, there can be mentioned, but not limited to, promoters such as *E. coli* lactose (lac) and *E. coli* trp. All of the above promoters have already been characterized and are well known to a person skilled in the art, and can be assembled either synthetically or from known plasmids.

The illustrated DNA sequence of the present invention, plasmids and viruses may have many modifications and variations. For example, due to degeneracy of genetic code, nucleotide substitution can be made throughout the coding region of a polypeptide. Such a sequence can be easily deduced from the nucleotide sequence of ChM1L gene of the present invention or the amino acid sequence encoded by the gene, and can be assembled by a conventional synthetic method described below. Such a synthetic method may be substantially carried out according to Itakura's method (Itakura et al., Science, 198, 1059, 1977) and Crea's method (Crea et al., Proc. Natl. Acad. Sci. USA 75, 5765, 1978). Thus the present invention is not limited to the specifically illustrated nucleotide sequences, plasmids or viruses.

As methods of introducing the desired recombinant DNA of the present invention into a host cell and the following transforming method, various conventional methods may be used. The transformant obtained may be cultured according to a standard method, from which culture the polypeptide encoded by the ChM1L gene of the present invention can be produced. As the culture medium used for this culturing, a commonly used medium may be selected as appropriate depending on the host cell adopted, and culturing may be carried out under a condition suitable for the growth of the host cell.

From the foregoing, the above polypeptide can be produced intracellularly, extracellularly, or on the cell membrane of the transformant. Said polypeptide can be separated and purified utilizing, as desired, the physical properties, chemical properties thereof or the like by various separation procedures ["Biochemistry Databook II", pp. 1175-1259, First edition, First Print, Jun. 23, 1980, Tokyo Kagaku Dojin; Biochemistry, 25 (25), 8274-8277 (1986); Eur. J. Biochem., 163, 313-321 (1987), and the like]. Specific examples of said methods include, for example, commonly used reconstitution treatment, treatment with a polypeptide precipitating agent (salting out), centrifugation, osmotic shock, ultrasonic disruption, ultrafiltration, gel filtration, various chromatographic methods such as adsorption chromatography, ion exchange chromatography, affinity chromatography and high performance liquid chromatography (HPLC), and combinations thereof. Furthermore, by allowing the expression of the protein in which an affinity tag was fused to said polypeptide, the tag can be used to perform affinity purification. As the affinity tag as used herein, there can be mentioned a polyhistidine tag (His tag, Sisk et al., J. Virol., 68, 766, 1994) and a FLAG tag (Hopp et al., Biotechnology 6, 1204-1210, 1988). The expression and detection of the ChM1L polypeptide fused to these affinity tags can be performed as described in Examples 8 and 9, and it is also possible to purify the ChM1L polypeptide using these tags.

The method of producing the polypeptide encoded by the ChM1L of the present invention is outlined as follows, though more detailed explanations thereof will be made hereinafter in Example 8.

The human and mouse ChM1L gene of the present invention and a gene encoding the ChM1L protein in which a His tag is fused at the C-terminal were cloned into pcDNA3.1(+) vector (Example 4), which was then transfected into COS7 cells. About 48 hours later, the culture supernatant and the cellular components were harvested and were subjected to a Western blot method in order to detect a ChM1L recombinant protein. However, in any of the culture supernatant and the cellular components no expression of ChM1L protein was detected.

Therefore, conditions for detecting the expression of ChM1L recombinant proteins were investigated, and it was found that the use of pCAGGS as the expression vector enables the detection of expression of said polypeptide in COS7 cells. The human and mouse ChM1L gene of the present invention and a gene encoding the ChM1L protein in which a His tag is fused at the C-terminal were cloned into pCAGGS vector (Example 4), which was transfected into COS7 cells. About 48 hours later, the culture supernatant and the cellular components were harvested and were subjected to a Western blot method in order to detect ChM1L recombinant proteins. No expression of ChM1L recombinant proteins was confirmed in the culture supernatant, whereas in the cellular components two bands were detected at around 40 kDa.

Figure 6:
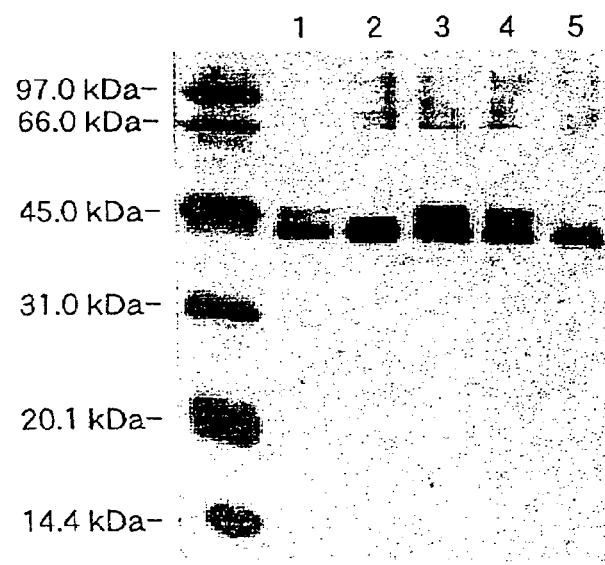
FIG. 6 shows the result in which mouse ChM1L (His-tagged) protein was expressed in COS7 cells, and after the cellular components were recovered they were subjected to a deglycosylation, and the ChM1L protein was detected by Western blot using anti-His tag antibody followed by the analysis of glycosylations. Lane 1 represents the result of Western blot of a non-treated sample, lane 2 represents that of a NANase II + O-glycosidase DS + PNGase-treated sample, lane 3 represents that of a NANase II-treated sample, lane 4 represents that of an O-glycosidase DS-treated sample, and lane 5 represents that of a PNGase-treated sample.

Thus, it was revealed that the ChM1L protein is a membrane-bound protein. On the other hand, it has been confirmed that when ChM-I is expressed in COS7 cells, it is secreted as a soluble protein in the culture supernatant (Hiraki et al., J. Biol. Chem., 272, 32419-32426, 1997). Thus the analysis with COS7 cells revealed that ChM1L and ChM-I are proteins having different structures. That is, it was shown that ChM1L is a cell membrane-bound protein, while ChM-I is a secretary protein, and that the processing mechanisms of these molecules are different. Among the two bands for the ChM1L protein, the band at the high molecular weight was found to be a form modified by a N-linked sugar chain in the Example 10 described below (FIG. 6).

The ChM1L protein thus expressed can affinity purified using a ChM1L-specific antibody or an antibody against the tag (His tag) in which 6 residues of histidine are fused, a nickel column and the like.

The polypeptide encoded by the ChM1L gene of the present invention may be any of a membrane-bound polypeptide and a soluble polypeptide having no property of binding to the cell membrane. For example, there may be cases in which after the polypeptide is expressed as a membrane-bound polypeptide on the cell membrane, it is cleaved to become a soluble polypeptide. Though the ChM1L protein was detected as a membrane-bound protein in the expression in COS7 cells (Example 8), it may undergo processing thereby to be a soluble protein when the host cell or the culture condition is different. Furthermore, the soluble polypeptide that lacks the transmembrane domain can be expressed by fusing a heterologous signal peptide to the N-terminal.

More specifically, the method of expressing the soluble ChM1L protein is outlined as follows, though more detailed explanations thereof will be made hereinafter in Example 9.

A vector was constructed that has integrated, into pCAGGS vector, a nucleotide sequence encoding a protein in which the signal sequence of preprotrypsin, a FLAG tag, the C-terminal end of the extracellular region of ChM1L were fused from the N-terminal end (Example 5). The ChM1L protein that was expressed using this vector was secreted into the culture liquid as a soluble protein after the signal sequence of preprotrypsin was cleaved (Example 9, FIG. 5).

The soluble ChM1L polypeptide thus secreted into the culture liquid can be purified using anti-ChM1L antibody or anti-FLAG antibody (Sigma) because a FLAG tag is fused thereto. It is also possible to remove the FLAG tag by cleaving the FLAG fusion protein with enterokinase.

More specifically, the method of purifying the soluble ChM1L protein is outlined as follows though more detailed explanations thereof will be made hereinafter in Example 13.

Figure 8:
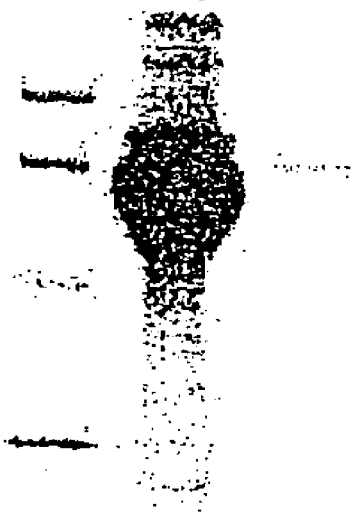
FIG. 8 shows the result in which a soluble human ChM1L protein that was expressed in the culture liquid of COS7 cells was purified by affinity chromatography using anti-FLAG M2 affinity gel, electrophoresed, and stained with Coomassie brilliant blue. Lane 1 shows the result of electrophoresis of the culture supernatant of COS7 cells and lane 2 shows that of the purified ChM1L protein.

Using a Lipofectamine reagent (GIBCO BRL) according to the instruction attached to the product, pSF-shChM1L was transfected into COS7 cells, and 48 hours later the culture supernatant was harvested. From this culture supernatant, a soluble ChM1L protein was purified by affinity chromatography using anti-FLAG M2 affinity gel (Sigma) (FIG. 8).

The ChM1L polypeptide of the present invention can be used as a polypeptide-purifying reagent. Said polypeptide bound to a solid support is very useful for the purification of polypeptides that can bind to said peptide by affinity chromatography. As the polypeptide that can bind to the ChM1L polypeptide, there may be illustrated soluble polypeptides, membrane-bound polypeptides, antibodies and the like. The soluble ChM1L polypeptide may be readily used for the addition into the cell culture liquid in vitro, or intravenous administration in vivo.

In order to search the activity of the ChM1L polypeptide of the present invention, human umbilical vein endothelial cells (HUVECs) were used to analyze the presence of a angiogenesis-inhibiting activity. More specifically, the method is outlined as follows though more detailed explanations thereof will be made hereinafter in Example 14. When HUVECs are cultured on a plate coated with Matrigel (Becton Dickinson), vascular endothelial cells form a tube-like structure (FIG. 9). When the ChM1L polypeptide purified by the above-mentioned affinity chromatography is added to the culture liquid, the formation of tube-like structure of HUVECs was inhibited (FIG. 9). Therefore, it is clear that ChM1L has a angiogenesis-inhibiting activity, and that the soluble ChM1L polypeptide can be applied as a therapeutic agent for diseases accompanied by angiogenesis such as diabetic retinopathy, cancer, and rheumatoid arthritis.

Using the polypeptide encoded by the ChM1L gene of the present invention, a specific antibody can be generated. An antigen as used herein includes a polypeptide produced in large quantities according to the above genetic engineering method or a chemically synthesized polypeptide, and an antibody obtained may be any of polyclonal antibody or monoclonal antibody, and can be effectively used for the purification, measurement, recognition, and the like of said polypeptide. Hence, polyclonal antibodies and monoclonal antibodies against said polypeptide can be used for treatment or the development of therapeutic methods for diseases that are mediated (directly or indirectly) by said polypeptide, and can also be used as diagnostic reagents for the above diseases.

Antibodies that specifically bind to the polypeptide encoded by the ChM1L gene of the present invention can be generated as shown in Example 7. That the generated anti-ChM1L polypeptide antibody specifically binds to said polypeptide was confirmed in the result of Western blot shown in Example 8 (FIG. 4).

Anti-ChM1L polypeptide antibody may also be used for immunostaining tissue sections as described in Example 11. When a rib cartilage was stained with an anti-ChM1L polypeptide antibody, cells that assume a fibroblast-like flat form occurring in such a way as to surround the cartilaginous tissue were specifically stained (FIG. 7). On the other hand, it has been demonstrated that ChM-I is specifically expressed on chondrocytes and immunostaining has also shown that it is accumulated in the chondrocytes and matrices other than the chondrocytes (Hiraki et al., J. Biol. Chem., 272, 32429-32426, 1997). It was therefore revealed that ChM1L and ChM-I are expressed in different cells in the tissue including cartilage, which thereby demonstrated that ChM1L and ChM-I are molecules that have different functions.

The tissue containing the cell group exhibiting a fibroblast-like form that was demonstrated to be expressing the ChM1L protein by immunostaining is conventionally termed as perichondrium (Suda et al., Bone Formation and Bone Absorption and their regulating factors 1, 2, 1995). Though there is no definite definition at present on the tissue perichondrium, it is herein intended to mean a tissue containing cell groups that exhibit a fibroblast-like form.

The cells present in the perichondrium are thought to be a source for chondrocytes that are required for the development of cartilaginous tissues during the process of endochondral bone formation. Hence, the perichondrium is an important tissue that supplies chondrocytes at the time of skeleton formation during the process of development or bone and cartilage injuries in adults. Furthermore, though the cartilaginous tissue is characterized in that there are no blood vessels, nerves, or lymphatic vessels, the perichondrium is thought to regulate the infiltration of blood vessels, nerves, or lymphatic vessels into the chondrocytes since the perichondrium is present at the interface of cartilaginous tissues and other tissues. Thus, though perichondrium is recognized to be an important tissue, it has no definite definition and detailed study has not been made at present. One reason for this that there are no molecules that are perichondrium-specifically expressed have been elucidated at all.

Accordingly, if the presence of molecules that are specifically expressed in the tissue termed as perichondrium surrounding the cartilaginous tissue is demonstrated, it would provide a very important tool in the study of perichondrium and cartilaginous tissues.

The ChM1L of the present invention is the only molecule that was demonstrated to be perichondrium-specifically expressed, and is thought to regulate the infiltration of blood vessels, nerves, or lymphatic vessels into the cartilaginous tissues.

Hence, the discovery of the ChM1L gene and the result of functional analysis of ChM1L included herein is believed to provide, from now on, a new perspective on the etiology and the development of therapeutic methods for diseases in which perichondrium and other ChM1L-expressing tissues including the cartilaginous tissue are involved.

Thus, the ChM1L gene and the ChM1L polypeptide of the present invention, antagonists and agonists to ChM1L including antibody that binds to ChM1L, and agents that promote or reduce the expression of the ChM1L gene are considered to be used as therapeutic agents for diseases in which the above ChM1L-expressing cells are involved.

The above expression analysis of mRNA and the result of immunostaining revealed that the ChM1L gene and the polypeptide encoded thereby of the present invention are expressed in the brain, the eyeball, the skeletal muscle, the thyroid, the whole rib including cartilage, the kidney, the stomach, the trachea, and cells that assume a fibroblast-like flat form occurring in such a way as to surround the cartilaginous tissue. It suggests, therefore, that the ChM1L gene and the polypeptide encoded thereby of the present invention may be involved in diseases associated with the above tissues that have been confirmed to express them, such as diabetic retinopathy, muscular dystrophy, Basedow's disease, chronic kidney failure, stomach cancer, chronic bronchitis, osteoarthritis and rheumatoid arthritis.

Hence, the ChM1L gene and the ChM1L polypeptide of the present invention, antagonists and agonists to ChM1L including antibody that binds to ChM1L, and agents that promote or reduce the expression of the ChM1L gene are considered to be used as therapeutic agents for these diseases.

EXAMPLES

The present invention will now be explained more specifically with reference to the following examples. It should be noted, however, that the present invention is not limited to these examples.

Example 1

Analysis of the ChM1L Amino Acid Sequence

The homology of amino acid residues of ChM-I and ChM1L was compared (FIG. 1(a)). The amino acid sequence was represented by one alphabetical letter. ChM1L has a homology with ChM-I throughout the molecule, but it was found that ChM1L has a particularly high homology with the C-terminal of ChM-I that is extracellularly secreted following the processing of ChM-I.

The homology of amino acid sequences of human, mouse and rat ChM1L was compared (FIG. 1(b)). The ChM1L polypeptide is composed of 317 amino acids in humans, mice, and rats, but the 300 amino acid residues were identical in the three (about 95%).

The degree of hydrophobicity of ChM-I and ChM1L is shown in the figure (FIG. 2). In both of ChM-I and ChM1L, a large hydrophobic peak is observed in the N-terminal end. This hydrophobic region is characteristically observed in the cell membrane-bound proteins, and it was demonstrated that both of ChM1L and ChM-I are type II membrane-bound proteins.

Example 2

Cloning of the ChM1L Gene

Using the amino acid sequence (Genbank accession number M16441) of human ChM-I, TBLASTN search was performed for the Expressed sequence tag data base (dbEST) in the DNA data bank of Japan (DDBJ). As a result, an EST file, Genbank accession number AI123839 was detected as a novel gene fragment having a homology with ChM-I.

Using Clontech's Human fetus Marathon-Ready ™ cDNA, cDNA was amplified by the RACE method according to the instruction attached to the product. Primers were synthesized from the nucleotide sequence obtained from the above dbEST, and ExTaq polymerase (Takara Shuzo) was used according to the instruction attached to the product. Using GeneAmp™ PCR System 9700 (PE Applied Biosystems), PCR reaction was carried out for 30 cycles with each cycle comprising 96° C. for 30 seconds, 60° C. for 30 seconds, and 72° C. for one minute, and finally incubated at 72° C. for 6 minutes to obtain a PCR reaction mixture. One tenth of the reaction mixture was added, and the second PCR was performed in the same condition.

The PCR product obtained was subjected to electrophoresis on a 1% agarose gel containing ethidium bromide and then the gel was observed under UV irradiation to examine DNA bands. The amplified fragments were excised from the gel, and were purified using QIAquick Gel Extraction Kit (QIAGEN) according to the instruction attached to the product.

The nucleotide sequence of the purified fragment was determined using a DNA sequencer (ABI PRISM™ 310 Genetic Analyzer) of PE Applied Biosystems and ABI PRISM ™ BigDye Terminator Cycle Sequencing Ready Reaction kit.

The nucleotide sequence of human ChM1L cDNA is shown in SEQ ID NO: 1 and its amino acid sequence is shown in SEQ ID NO: 2.

Since the amino acid sequence encoded by the human ChM1L gene represented by SEQ ID NO: 1 has a homology with human ChM-I, the gene was decided to be termed as the ChM1L gene (ChM-I like gene).

The coding sequence (CDS) of Human ChM1L cDNA was amplified by PCR, electrophoresed on agarose, and then was purified, which was then cloned using pCR-Script™ Amp cloning kit (Stratagene) according to the instruction attached to the product. The sequence of the primers used in PCR are shown in SEQ ID NO: 7 (forward primer) and SEQ ID NO: 8 (reverse primer). The ChM1L gene sequence that has been integrated into the vector was determined using ABI PRISM™ 310 Genetic Analyzer of PE Applied Biosystems and ABI PRISM™ BigDye Terminator Cycle Sequencing Ready Reaction kit.

Using the amino acid sequence (SEQ ID NO: 2) of human ChM1L, TBLASTN search was carried out as described in the above human case. As a result, as a gene fragment that encodes mouse ChM1L, EST file, Genbank accession number AV009191 was detected, and as a gene fragment that encodes rat ChM1L, EST file, Genbank accession number AI112003 was detected. Using Mouse 11-day Embryo Marathon-Ready™ cDNA and Rat Skeletal muscle Marathon-Ready™ cDNA by Clontech, sequences of mouse and rat ChM1L genes were determined by the RACE method as described in the isolation of the human ChM1L gene.

The nucleotide sequence of mouse ChM1L cDNA is shown in SEQ ID NO: 3 and the amino acid sequence is shown in SEQ ID NO: 4. The nucleotide sequence of rat ChM1L cDNA is shown in SEQ ID NO: 5 and the amino acid sequence is shown in SEQ ID NO: 6.

The coding sequences (CDS) of mouse and rat ChM1L cDNA were amplified by PCR, and were purified after agarose electrophoresis, which were then cloned using pCR-Script™ Amp cloning kit (Stratagene) according to the instruction attached to the product. The sequences of the primers used in PCR of the mouse gene are shown in SEQ ID NO: 9 (forward primer) and SEQ ID NO: 10 (reverse primer). The sequences of the primers used in PCR of the rat gene are shown in SEQ ID NO: 11 (forward primer) and SEQ ID NO: 12 (reverse primer). The sequence of the ChM1L gene that was integrated into the vector was determined using ABI PRISM™ 310 Genetic Analyzer of PE Applied Biosystems and ABI PRISM™ BigDye Terminator Cycle Sequencing Ready Reaction kit.

The names of human, mouse and rat ChM1L genes constructed in this Example are abbreviated to:

the vector containing the human ChM1L gene: pCR-hChM1L the vector containing the mouse ChM1L gene: pCR-mChM1L the vector containing the rat ChM1L gene: pCR-rChM1L Example 3

Construction of Vectors Containing Genes Encoding Human and Mouse ChM1L Proteins in which 6 Residues of Histidine are Fused to the C-Terminal The coding sequences (CDS) of human and mouse ChM1L cDNA were amplified by PCR, and were purified after agarose electrophoresis, which were then cloned using pCR-Script SK(+) vector that has been improved so that 6 histidine residues (His tag) may be fused to the C-terminal and pCR-Script™ Amp cloning kit (Stratagene) according to the instruction attached to the product. The sequence of the primers used in PCR of the human gene are shown in SEQ ID NO: 7 (forward primer) and SEQ ID NO: 13 (reverse primer). The sequence of the primers used in PCR of the mouse gene are shown in SEQ ID NO: 9 (forward primer) and SEQ ID NO: 14 (reverse primer). That a nucleotide sequence encoding a protein in which His tags are fused to the C-terminal of ChM1L was determined using ABI PRISM™ 310 Genetic Analyzer (PE Applied Biosystems) and ABI PRISM™ BigDye Terminator Cycle Sequencing Ready Reaction kit according to the instruction attached to the product. The amino acid sequences of human and mouse ChM1L in which His tags were fused to the C-terminal are shown in SEQ ID NO: 17 and 18, and the nucleotide sequence encoding them are shown in SEQ ID NO: 15 and 16.

The genes encoding the ChM1L protein constructed in this Example in which a His tag was fused are abbreviated to:

the vector containing a gene encoding the protein in which human ChM1L and His tags were fused: pCR-hChM1LHis the vector containing a gene encoding the protein in which mouse ChM1L and His tags were fused: pCR-mChM1LHis Example 4

Construction of Expression Vectors

In order to express the ChM1L gene in a mammalian cell, CDSs were excised from the above pCR-hChM1L, pCR-mChM1L, pCR-hChM1LHis, and pCR-mChM1LHis with restriction enzymes EcoRI and NotI, were electrophoresed on agarose, and then the desired bands were purified, which were ligated to pcDNA3.1(+) (Invitrogen) and pCAGGS (Gene, 108, 193-200, 1991) using Ligation high (Toyobo) according to the instruction attached to the product. The solutions after the ligation reaction were subjected to transformation using E. coli JM109 competent cells (Takara Shuzo) according to the instruction attached to the product. After purifying the plasmids, the integration of the desired gene was confirmed by restriction enzyme reactions and agarose electrophoresis.

The vectors constructed in this Example are abbreviated to:

pcDNA3.1(+) vectors containing the hChM1L, mChM1L, hChM1LHis and mChM1LHis: pcDNA-hChM1L, pcDNA-mChM1L, pcDNA-hChM1LHis, and pcDNA-mChM1LHis pCAGGS vectors containing the hChM1L, mChM1L, hChM1LHis and mChM1LHis: pCAGGS-hChM1L, pCAGGS-mChM1L, pCAGGS-hChM1LHis, and pCAGGS-mChM1LHis Example 5

Construction of Vectors that Express Human Soluble ChM1L Protein to which a FLAG Tag is Fused The FLAG tag (Sigma) as used herein is a hydrophilic marker peptide comprising eight amino acids (Asp Tyr Lys Asp Asp Asp Asp Lys), and the last five amino acids (Asp Asp Asp Asp Lys) is a recognition sequence for enterokinase. The vectors constructed in this Example can express a protein in which the signal sequence of preprotrypsin, a FLAG tag, the C-terminal end of the extracellular region of ChM1L were fused from the N-terminal end. The protein that was expressed using this vector is secreted into the culture liquid as a soluble protein after the signal sequence of preprotrypsin is cleaved, as explained in detail hereinafter in Example 9. Since a FLAG tag is fused to the protein expressed with this vector, the protein can be purified using anti-FLAG antibody (Sigma) and by cleaving the fusion protein with enterokinase, the FLAG tag can also be removed.

A vector was constructed in which a nucleotide sequence (SEQ ID NO: 19, contained in pFLAG-CMV-1 vector manufactured by Sigma) encoding the signal sequence of preprotrypsin and a FLAG tag (SEQ ID NO: 20) from the N-terminal was integrated into the pCAGGS vector (hereinafter referred to as pSF vector). A nucleotide sequence (nucleotide sequence No. 684 to 1020 of SEQ ID NO: 1) encoding the amino acids No. 212 to 317 of human ChM1L represented by SEQ ID NO: 2 and the translation termination codon was amplified by the PCR method, and the amplified product was integrated into the 3'-end of the nucleotide sequence encoding the FLAG tag of the pSF vector. The sequences of primers used for PCR are shown in SEQ ID NO: 21 (forward primer) and SEQ ID NO: 8 (reverse primer). The integration of the sequence of interest into the constructed vector was confirmed using a ABI PRISM™ 310 Genetic Analyzer (PE Applied Biosystems) and ABI PRISM™ BigDye Terminator Cycle Sequencing Ready Reaction kit according to the instruction attached to the product. The nucleotide sequence of this Example integrated into the vector is shown in SEQ ID NO: 22, and the amino acid sequence encoded thereby is shown in SEQ ID NO: 23. The vector constructed in this Example will be abbreviated to pSF-shChM1L.

Example 6

Expression Analysis of ChM1L mRNA Expression Analysis of ChM1L mRNA in Various Tissues of an Adult (10-Week Old): FIG. 3(a)

A 10-week old C57BL/6 mouse was dissected and each tissue was extracted, which was immediately frozen in liquid nitrogen. The frozen tissue was ground into small pieces, and using IOSGEN (Nippon Gene) according to the instruction attached to the product the total RNA of each tissue was obtained. With one µg of total RNA of each tissue as template, 20 µl of cDNA was synthesized using Superscript II preamplification kit (GIBCO BRL) according to the instruction attached to the product. In RT-PCR, the total liquid volume of the reaction system was set at 50 µl, and for each tissue 0.5 µl of cDNA, 0.25 µl of ExTaq polymerase (Takara Shuzo) were used, to which the forward primer (SEQ ID NO: 9) and the reverse primer (SEQ ID NO: 10) were added to a concentration of 0.2 µm. Using GeneAmp™ PCR System 9700 (PE Applied Biosystems), PCR amplification was performed for 30 cycles with each cycle comprising 96° C. for 30 seconds, 60° C. for 30 seconds, and 72° C. for one minute. The reaction mixture obtained was subjected to electrophoresis on a 1% agarose gel containing ethidium bromide and then the gel was observed under UV irradiation to examine the expression of ChM1L mRNA in each tissue.

As shown in FIG. 3(a), the expression of ChM1L mRNA in each tissue of an adult mouse was observed in the brain, the eyeball, the skeletal muscle, the whole rib, and the thyroid. The expression of ChM-I in mice has been confirmed in the eyeball, the thymus, the cartilage, and the whole rib. It is therefore clear that ChM1L and ChM-I are expressed in different tissues in the living body, suggesting that their physiological functions are different.

Expression Analysis of ChM1L mRNA in Various Tissues of a Fetus (Day 17 of Gestation): FIG. 3(b)

A fetus of C57BL/6 mouse on day 17 of gestation was removed by Caesarean section. Each tissue was taken out, and was immediately frozen in liquid nitrogen. The extraction of total RNA from the frozen tissue, cDNA synthesis, and RT-PCR were performed as described in the above <Expression analysis of ChM1L mRNA in various tissues of an adult mouse>.

As shown in FIG. 3(b), the expression of ChM1L mRNA in each tissue of a fetus mouse was observed in the eyeball, the kidney, the stomach, the whole rib, and the trachea. In the fetus, expression in the kidney and the stomach was observed, in which no expression was observed in the adult mouse. It is therefore likely that ChM1L is involved in the development and morphogenesis of these organs, and is also considered to be involved in the repair and regeneration of organs. It was also revealed that ChM1L mRNA is expressed in the trachea.

Expression Analysis of ChM1L mRNA during the Developmental Stage of a Fetus: FIG. 3(c)

A fetus of C57BL/6 mouse on each day from day 10 of gestation to childbirth was removed by Caesarean section. Each the whole fetuses was frozen in liquid nitrogen. The extraction of total RNA from the frozen fetus, cDNA synthesis, and the implementation of RT-PCR were performed as described in the above <Expression analysis of ChM1L mRNA in various tissues of an adult mouse>.

The analysis of ChM-I mRNA was carried out using a fusion protein (SEQ ID NO: 23) and a reverse primer (SEQ ID NO: 24) under the same condition as above.

As shown in FIG. 3(c), the expression of ChM1L mRNA during the developmental stage of the fetus is very weak on day 10 of gestation and is increased in expression on days 11 to 13. On the other hand, though the expression of ChM-I was also increased as for ChM1L, it exhibited an evidently stronger expression than ChM1L on days 10 and 11 of gestation. It is therefore clear that the expression of ChM1L lags behind ChM-I during the developmental stage of the fetus, and that these molecules have different functions in the fetus development.

Example 7

Generation of Anti-ChM1L Peptide Polyclonal Antibody

A peptide having cysteine at the C-terminal of the sequence from 245 to 252 residues shown in SEQ ID NO: 2 of human ChM1L was chemically synthesized. To this synthetic peptide, MBS/KLH (m-maleimidobenzoyl-N-hydroxysuccinimide ester/keyhole limpet hemocyanin, Boehringer Mannheim) was coupled. After the complex was dissolved in physiological saline, an equal amount of Freund's complete adjuvant (FCA) was added, which was sonicated to prepare an emulsion. This emulsion was subcutaneously given to a rabbit as the initial immunization. Four weeks after the initial immunization, a booster immunization was carried out using Freund's incomplete adjuvant (FIA) to the femoral muscle, and thereafter immunization by subcutaneous administration was carried out for four times at an interval of about two weeks or four weeks. During the booster immunization, blood was partially taken from the auricle, and after the final immunization the entire blood was taken and serum was separated. By affinity purification using a peptide column, an anti-ChM1L peptide polyclonal antibody was obtained.

Example 8

Analysis of Human and Mouse ChM1L Recombinant Protein by Western Blotting: FIG. 4

Using the lipofectamine reagent (GIBCO BRL) according to the instruction attached to the product, pCAGGS, pCAGGS-hChM1L and pCAGGS-mChM1L (FIGS. 4(a) and (c)), or pCAGGS, pCAGGS-hChM1LHis and pCAGGS-mChM1LHis (FIGS. 4(b) and (d)) were transfected into COS7 cells. About 48 hours after the transfection, the culture supernatant and the cellular components were subjected to sodium dodecyl sulfate-polyacrylamide gel electrophoresis (SDS-PAGE) on a 12.5% gel, and then transferred to a nitrocellulose membrane. A primary antibody reaction and a secondary antibody reaction were carried out, and then subjected to a color developing reaction using the ECLplus reagent (Amersham Pharmacia Biotech) according to the instruction attached to the product. In the Western blot in which pCAGGS, pCAGGS-hChM1L and pCAGGS-mChM1L were transfected, anti-ChM1L polyclonal antibody described in the above Example was used as the primary antibody and horseradish peroxidase (HRP)-labelled anti-rabbit IgG antibody (DAKO) was used as the secondary antibody, and in the Western blot in which pCAGGS, pCAGGS-hChM1LHis and pCAGGS-mChM1LHis were transfected, anti-His tag antibody (Invitrogen) was used as the primary antibody and HRP-labelled anti-mouse IgG antibody (Amersham Pharmacia Biotech) was used as the secondary antibody.

SDS-PAGE was carried out for the same samples as in Western blot, and the results of staining with Coomassie brilliant blue (CBB) are shown in FIGS. 4(a) and (b).

As a result of Western blot, no ChM1L band was confirmed in any of the culture supernatants. In cellular components, as shown in FIGS. 4(b) and (d), recombinant ChM1L protein was detected as two bands at around 40 kDa whether anti-ChM1L peptide antibody or anti-His tag antibody was used. As will be described in detail in the Examples below, the band at the high molecular weight was confirmed to be a form in which a N-linked glycosylation.

Example 9

Figure 5:
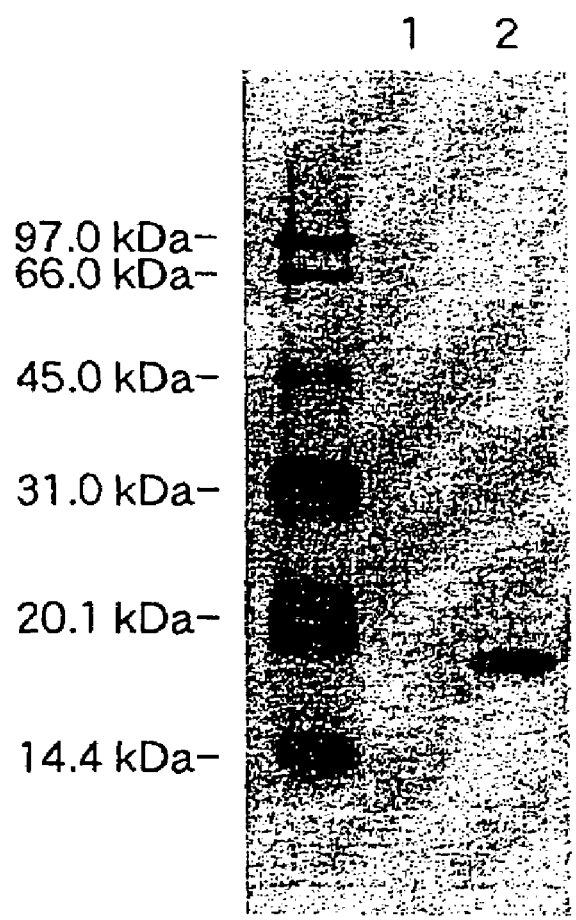
FIG. 5 shows the result in which soluble ChM1L (lane 2) and Mock (lane 1) expressed in COS7 cells were detected by Western blot using anti-FLAG M2 antibody.

Analysis of Soluble Human ChM1L Recombinant Protein by a Western Blot Method: FIG. 5

Using the lipofectamine reagent (GIBCO BRL) according to the instruction attached to the product, pCAGGS and pSF-shChM1L were transfected into COS7 cells. After the culture supernatants were subjected to SDS-PAGE on a 12.5% gel, they were transferred to a nitrocellulose membrane. Anti-FLAG M2 antibody (Sigma) was used as the primary antibody and HRP-labelled anti-mouse IgG antibody (DAKO) was used as the secondary antibody, and the ECLplus reagent (Amersham Pharmacia Biotech) was used according to the instruction attached to the product to perform color development reaction.

As shown in FIG. 5, soluble human ChM1L protein was detected as a single band at around 17-18 kDa.

Example 10

Deglycosylation Analysis of ChM1L Recombinant Protein

Using the lipofectamine reagent (GIBCO BRL) according to the instruction attached to the product, pCAGGS-mChM1LHis was transfected into COS7 cells. After PBS saline containing 2% SDS was added to a dish, cells were harvested by a scraper, and the suspension was heated at 95° C. for 60 minutes. The supernatant was treated with SDS-OUT™ SDS Precipitation kit (Pierce) to remove SDS. Using the protein solution thus obtained, a deglycosylation was carried out using the Enzymatic Deglycosylation Kit (BIO RAD) according to the instruction attached to the product to treat the above protein solution with NANase II, O-glycosidase DS and PNGase F. After the reaction mixture was subjected to SDS-PAGE on a 12.5% gel, it was transferred to a nitrocellulose membrane. Anti-His tag antibody (Invitrogen) was used as the primary antibody and HRP-labelled anti-mouse IgG antibody (Amersham Pharmacia Biotech) was used as the secondary antibody, and the ECLplus reagent (Amersham Pharmacia Biotech) was used according to the instruction attached to the product to perform color development reaction.

As shown in FIG. 6, the band of ChM1L protein at the high molecular weight disappeared only when treated with pNGase F (lanes 2 and 5). It was therefore demonstrated that the ChM1L protein has been modified with a N-linked sugar chain.

Example 11

Analysis of ChM1L Protein at Cartilago Costalis by Immunostaining

An about 10-week old C57BL/6 mouse was dissected to remove the whole rib, which was fixed in a 10 mM phosphate buffer (pH 7.4) (PBS) containing 4% paraformaldehyde, embedded in paraffin, and then sections were prepared. Each step of immunostaining was carried out using Histfine SAB-PO® kit (Nichirei) according to the instruction attached to the product, of which outline is as follows: After deparaffinization, endogenous peroxidase was digested with a 3% hydrogen peroxide. After washing with PBS followed by blocking with 10% normal goat serum, the above-mentioned anti-ChM1L peptide antibody at a dilution of 1/160 was added and incubated overnight at 4° C. As a negative control, rabbit IgG was used. After biotin-labelled anti-rabbit IgG antibody and peroxidase-labelled streptoavidin were allowed to react, 3,3-diaminobendizine/4HCl was added to perform a color development reaction. The nucleus was stained with haematoxylin, enclosed, and then observed.

As shown in FIG. 7, ChM1L protein is expressed in cells that assume a fibroblast-like flat form occurring in such a way as to surround the cartilaginous tissue. On the other hand, there were no expressions observed in the cartilage cell in which the expression of ChM-I has been reported.

Example 12

Chromosome Mapping of the Human ChM1L Gene

Using the gene sequence (SEQ ID NO: 1) of human ChM1L, BLASTN search was performed for the entire DDBJ data from the DNA data bank of Japan (DDBJ). As a result, Genbank accession number AL035608 was detected as the genome sequence of the ChM1L gene. AL035608 is a sequence mapped on chromosome X. It is therefore clear that the human ChM1L gene is present on chromosome X.

Example 13

Purification of a Soluble Human ChM1L Recombinant Protein

Using a Lipofectamine reagent (GIBCO BRL) according to the instruction attached to the product, pSF-shChM1L was transfected into COS7 cells, and 48 hours later the culture supernatant was harvested. Using anti-FLAG M2 affinity gel (Sigma), an affinity column was prepared, and the culture supernatant was applied to the column. After washing the column three times in 25 mM Tris-HCl, 150 mM NaCl (pH 7.4), it was eluted with 0.1 M glycine-HCl (pH 3.5), and the eluent was neutralized with a 1/20 volume of 1M Tris-HCl (pH 9.5).

The culture supernatant and the eluent were subjected to SDA-PAGE and then were stained with Coomassie brilliant blue (CBB), the result of which is shown in FIG. 8. Though there are a variety of proteins in the culture supernatant (FIG. 8, lane 1), soluble human ChM1L protein was confirmed as an about 20 kDa band in the eluent. This revealed that soluble human ChM1L protein was concentrated and purified by the above procedure (FIG. 8, lane 2).

Example 14

Study on the Effect of Inhibiting Angiogenesis using Human Umbilical Vein Endothelial Cells Human umbilical vein endothelial cells (HUVECs, Clonetics) were cultured in a exclusive medium (EGM™-2 Bullet Kit™, Clonetics) for endothelial cells. To a 12-well plate, Growth factor reduced Matrigel (Becton Dickinson) was added to 600 μl/well, which was then incubated at 37° C. for 30 minutes. Using a heparin-free exclusive medium for endothelial cells diluted 1/8 in the essential medium (EBM™-2, Clonetics) for endothelial cells, a cell suspension containing $5 \times 10^4$ cells/ml of HUVECs were prepared.

Each test substance solution was prepared as a solution in which a 1/20 volume of 1M Tris-HCl (pH 9.5) was added to 0.1M glycine-HCl (pH 3.5), and 200 μl/well of it was treated. The above buffer and bovine serum albumin (BSA) at 20 μg/well as the negative control, platelet factor 4 (PF-4, CHEMICON) at 1 and 10 μg/well as the positive control, and the eluted fractions of Example 13 at 10 and 20 μg/well as the soluble human ChM1L recombinant protein were treated. Two ml of the cell suspension ($1 \times 10^5$ cells) and 200 μl of the test substance solution were mixed, and seeded into a 12-well plate coated with Growth factor reduced Matrigel. Nine hours later, the formation of tube-like structures was examined and were a photograph was taken. The result is shown in FIG. 9. In the negative control, HUVECs formed tube-like structures (FIGS. 9(*a*) and (*b*)), but when ChM1L at 20 μg/well (FIG. 9(*d*)) was treated the formation of tube-like structures was inhibited as compared to the negative control.

It was therefore revealed that ChM1L has an effect of inhibiting angiogenesis and thus the soluble ChM1L polypeptide can be used as a therapeutic agent for disease accompanied by angiogenesis such as diabetic retinopathy, cancer, and rheumatoid arthritis.

What is claimed is:

1. A monoclonal antibody or an antigen-binding fragment thereof which specifically binds to a protein consisting of amino acids 202 to 317 of SEQ ID NO: 2.

2. An isolated polyclonal antibody or an antigen-binding fragment thereof which specifically binds to a protein consisting of amino acids 202 to 317 of SEQ ID NO: 2.

3. A hybridoma producing a monoclonal antibody or an antigen-binding fragment thereof, obtainable by cell fusion of a myeloma cell and an antibody-producing cell immunized with a protein consisting of amino acids 202 to 317 of SEQ ID NO: 2.

4. A kit comprising (1) a protein consisting of amino acids 202 to 317 of SEQ ID NO: 2, and (2) a monoclonal antibody or antigen-binding fragment thereof, and/or a polyclonal antibody or antigen-binding fragment thereof, which specifically binds to said protein.

5. A composition comprising a monoclonal antibody or antigen-binding fragment thereof, or a polyclonal antibody or antigen-binding fragment thereof, which specifically binds to a protein consisting of amino acids 202 to 317 of SEQ ID NO: 2, and at least one carrier.

6. A composition comprising a monoclonal antibody or antigen-binding fragment thereof, or a polyclonal antibody or antigen-binding fragment thereof, which specifically binds to a protein consisting of amino acids 202 to 317 of SEQ ID NO: 2, and at least one carrier.

* * * * *

UNITED STATES PATENT AND TRADEMARK OFFICE
CERTIFICATE OF CORRECTION

PATENT NO.      : 7,575,922 B2                              Page 1 of 1
APPLICATION NO. : 11/196618
DATED           : August 18, 2009
INVENTOR(S)     : Yamana et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 507 days.

Signed and Sealed this

Seventh Day of September, 2010

David J. Kappos
*Director of the United States Patent and Trademark Office*

SEQUENCE LISTING

<160> NUMBER OF SEQ ID NOS: 25

<210> SEQ ID NO 1
<211> LENGTH: 1200
<212> TYPE: DNA
<213> ORGANISM: Homo sapiens

```
<220> FEATURE:
<221> NAME/KEY: CDS
<222> LOCATION: (67)..(1020)
<223> OTHER INFORMATION:

<400> SEQUENCE: 1
ctccacctca gcaggtgtct ctcagtcctc tcaaagcaag gaaagagtac tgtgtgctga        60 gagacc atg gca aag aat cct cca gag aat tgt gaa gac tgt cac att          108
       Met Ala Lys Asn Pro Pro Glu Asn Cys Glu Asp Cys His Ile
         1               5                  10 cta aat gca gaa gct ttt aaa tcc aag aaa ata tgt aaa tca ctt aag          156
Leu Asn Ala Glu Ala Phe Lys Ser Lys Lys Ile Cys Lys Ser Leu Lys
 15                  20                  25                  30 att tgt gga ctg gtg ttt ggt atc ctg gcc cta act cta att gtc ctg          204
Ile Cys Gly Leu Val Phe Gly Ile Leu Ala Leu Thr Leu Ile Val Leu
                     35                  40                  45 ttt tgg ggg agc aag cac ttc tgg ccg gag gta ccc aaa aaa gcc tat          252
Phe Trp Gly Ser Lys His Phe Trp Pro Glu Val Pro Lys Lys Ala Tyr
                 50                  55                  60 gac atg gag cac act ttc tac agc aat gga gag aag aag aag att tac          300
Asp Met Glu His Thr Phe Tyr Ser Asn Gly Glu Lys Lys Lys Ile Tyr
             65                  70                  75 atg gaa att gat cct gtg acc aga act gaa ata ttc aga agc gga aat          348
Met Glu Ile Asp Pro Val Thr Arg Thr Glu Ile Phe Arg Ser Gly Asn
 80                  85                  90 ggc act gat gaa aca ttg gaa gta cac gac ttt aaa aac gga tac act          396
Gly Thr Asp Glu Thr Leu Glu Val His Asp Phe Lys Asn Gly Tyr Thr
 95                 100                 105                 110 ggc atc tac ttc gtg ggt ctt caa aaa tgt ttt atc aaa act cag att          444
Gly Ile Tyr Phe Val Gly Leu Gln Lys Cys Phe Ile Lys Thr Gln Ile
                    115                 120                 125 aaa gtg att cct gaa ttt tct gaa cca gaa gag gaa ata gat gag aat          492
Lys Val Ile Pro Glu Phe Ser Glu Pro Glu Glu Glu Ile Asp Glu Asn
                130                 135                 140 gaa gaa att acc aca act ttc ttt gaa cag tca gtg att tgg gtc cca          540
Glu Glu Ile Thr Thr Thr Phe Phe Glu Gln Ser Val Ile Trp Val Pro
145                 150                 155 gca gaa aag cct att gaa aac cga gat ttt ctt aaa aat tcc aaa att          588
Ala Glu Lys Pro Ile Glu Asn Arg Asp Phe Leu Lys Asn Ser Lys Ile
    160                 165                 170 ctg gag att tgt gat aac gtg acc atg tat tgg atc aat ccc act cta          636
Leu Glu Ile Cys Asp Asn Val Thr Met Tyr Trp Ile Asn Pro Thr Leu
175                 180                 185                 190 ata tca gtt tct gag tta caa gac ttt gag gag gag gga gaa gat ctt          684
Ile Ser Val Ser Glu Leu Gln Asp Phe Glu Glu Glu Gly Glu Asp Leu
                    195                 200                 205 cac ttt cct gcc aac gaa aaa aaa ggg att gaa caa aat gaa cag tgg          732
His Phe Pro Ala Asn Glu Lys Lys Gly Ile Glu Gln Asn Glu Gln Trp
                210                 215                 220 gtg gtc cct caa gtg aaa gta gag aag acc cgt cac gcc aga caa gca          780
Val Val Pro Gln Val Lys Val Glu Lys Thr Arg His Ala Arg Gln Ala
                225                 230                 235 agt gag gaa gaa ctt cca ata aat gac tat act gaa aat gga ata gaa          828
Ser Glu Glu Glu Leu Pro Ile Asn Asp Tyr Thr Glu Asn Gly Ile Glu
    240                 245                 250 ttt gat ccc atg ctg gat gag aga ggt tat tgt tgt att tac tgc cgt          876
Phe Asp Pro Met Leu Asp Glu Arg Gly Tyr Cys Cys Ile Tyr Cys Arg
255                 260                 265                 270
```

```
cga ggc aac cgc tat tgc cgc gtc tgt gaa cct tta cta ggc tac    924
Arg Gly Asn Arg Tyr Cys Arg Arg Val Cys Glu Pro Leu Leu Gly Tyr
            275                 280                 285 tac cca tat cca tac tgc tac caa gga gga cga gtc atc tgt cgt gtc    972
Tyr Pro Tyr Pro Tyr Cys Tyr Gln Gly Gly Arg Val Ile Cys Arg Val
            290                 295                 300 atc atg cct tgt aac tgg tgg gtg gcc cgc atg ctg ggg agg gtc taa   1020
Ile Met Pro Cys Asn Trp Trp Val Ala Arg Met Leu Gly Arg Val
            305                 310                 315 taggaggttt gagctcaaat gcttaaactg ctggcaacat ataataaatg catgctattc   1080
aatgaatttc tgcctatgag gcatctggcc cctggtagcc agctctccag aattacttgt   1140
aggtaattcc tctcttcatg ttctaataaa cttctacatt atcaccaaaa aaaaaaaaaa   1200

<210> SEQ ID NO 2
<211> LENGTH: 317
<212> TYPE: PRT
<213> ORGANISM: Homo sapiens

<400> SEQUENCE: 2

Met Ala Lys Asn Pro Pro Glu Asn Cys Glu Asp Cys His Ile Leu Asn
1               5                   10                  15

Ala Glu Ala Phe Lys Ser Lys Lys Ile Cys Lys Ser Leu Lys Ile Cys
                20                  25                  30

Gly Leu Val Phe Gly Ile Leu Ala Leu Thr Leu Ile Val Leu Phe Trp
            35                  40                  45

Gly Ser Lys His Phe Trp Pro Glu Val Pro Lys Lys Ala Tyr Asp Met
        50                  55                  60

Glu His Thr Phe Tyr Ser Asn Gly Glu Lys Lys Lys Ile Tyr Met Glu
65                  70                  75                  80

Ile Asp Pro Val Thr Arg Thr Glu Ile Phe Arg Ser Gly Asn Gly Thr
                85                  90                  95

Asp Glu Thr Leu Glu Val His Asp Phe Lys Asn Gly Tyr Thr Gly Ile
            100                 105                 110

Tyr Phe Val Gly Leu Gln Lys Cys Phe Ile Lys Thr Gln Ile Lys Val
        115                 120                 125

Ile Pro Glu Phe Ser Glu Pro Glu Glu Glu Ile Asp Glu Asn Glu Glu
130                 135                 140

Ile Thr Thr Thr Phe Phe Glu Gln Ser Val Ile Trp Val Pro Ala Glu
145                 150                 155                 160

Lys Pro Ile Glu Asn Arg Asp Phe Leu Lys Asn Ser Lys Ile Leu Glu
                165                 170                 175

Ile Cys Asp Asn Val Thr Met Tyr Trp Ile Asn Pro Thr Leu Ile Ser
            180                 185                 190

Val Ser Glu Leu Gln Asp Phe Glu Glu Glu Gly Glu Asp Leu His Phe
        195                 200                 205

Pro Ala Asn Glu Lys Lys Gly Ile Glu Gln Asn Glu Gln Trp Val Val
    210                 215                 220

Pro Gln Val Lys Val Glu Lys Thr Arg His Ala Arg Gln Ala Ser Glu
225                 230                 235                 240

Glu Glu Leu Pro Ile Asn Asp Tyr Thr Glu Asn Gly Ile Glu Phe Asp
                245                 250                 255

Pro Met Leu Asp Glu Arg Gly Tyr Cys Cys Ile Tyr Cys Arg Arg Gly
            260                 265                 270

Asn Arg Tyr Cys Arg Arg Val Cys Glu Pro Leu Leu Gly Tyr Tyr Pro
        275                 280                 285
```

```
Tyr Pro Tyr Cys Tyr Gln Gly Gly Arg Val Ile Cys Arg Val Ile Met
        290                 295                 300

Pro Cys Asn Trp Trp Val Ala Arg Met Leu Gly Arg Val
305                 310                 315

<210> SEQ ID NO 3
<211> LENGTH: 1180
<212> TYPE: DNA
<213> ORGANISM: Mus musculus
<220> FEATURE:
<221> NAME/KEY: CDS
<222> LOCATION: (59)..(1012)
<223> OTHER INFORMATION:

<400> SEQUENCE: 3
agcagtagtc ctctcagtcc tctcaaagca gggaaagagc accgtgtgct gggagacc         58 atg gca aag aat cct cca gag aac tgt gag ggc tgt cac att cta aat       106
Met Ala Lys Asn Pro Pro Glu Asn Cys Glu Gly Cys His Ile Leu Asn
1               5                   10                  15 gca gaa gct ctg aaa tct aag aag ata tgt aaa tca ctg aag att tgt       154
Ala Glu Ala Leu Lys Ser Lys Lys Ile Cys Lys Ser Leu Lys Ile Cys
                20                  25                  30 gga cta gtg ttt ggt atc ctg gcc tta act cta att gtc ctg ttt tgg       202
Gly Leu Val Phe Gly Ile Leu Ala Leu Thr Leu Ile Val Leu Phe Trp
            35                  40                  45 ggg agc aaa cac ttc tgg ccc gag gta tcc aag aaa acc tat gac atg       250
Gly Ser Lys His Phe Trp Pro Glu Val Ser Lys Lys Thr Tyr Asp Met
        50                  55                  60 gag cac act ttc tac agc aac ggc gag aag aag aag att tac atg gaa       298
Glu His Thr Phe Tyr Ser Asn Gly Glu Lys Lys Lys Ile Tyr Met Glu
65                  70                  75                  80 att gat ccc ata acc aga aca gaa ata ttc aga agt gga aat ggc act       346
Ile Asp Pro Ile Thr Arg Thr Glu Ile Phe Arg Ser Gly Asn Gly Thr
                85                  90                  95 gat gaa aca ttg gaa gtc cat gac ttt aaa aat gga tac act ggc atc       394
Asp Glu Thr Leu Glu Val His Asp Phe Lys Asn Gly Tyr Thr Gly Ile
            100                 105                 110 tac ttt gta ggt ctt caa aaa tgc ttt att aaa act caa atc aaa gtg       442
Tyr Phe Val Gly Leu Gln Lys Cys Phe Ile Lys Thr Gln Ile Lys Val
        115                 120                 125 att cct gaa ttt tct gaa cca gag gaa gaa ata gat gag aat gaa gaa       490
Ile Pro Glu Phe Ser Glu Pro Glu Glu Glu Ile Asp Glu Asn Glu Glu
130                 135                 140 att act aca act ttc ttt gaa cag tca gtg att tgg gtt ccc gca gaa       538
Ile Thr Thr Thr Phe Phe Glu Gln Ser Val Ile Trp Val Pro Ala Glu
145                 150                 155                 160 aag cct att gaa aac aga gac ttc ctg aaa aat tct aaa att ctg gag       586
Lys Pro Ile Glu Asn Arg Asp Phe Leu Lys Asn Ser Lys Ile Leu Glu
                165                 170                 175 att tgc gat aat gtg acc atg tac tgg atc aat ccc act cta ata gca       634
Ile Cys Asp Asn Val Thr Met Tyr Trp Ile Asn Pro Thr Leu Ile Ala
            180                 185                 190 gtt tca gaa tta cag gac ttt gag gag gac ggt gaa gat ctt cac ttt       682
Val Ser Glu Leu Gln Asp Phe Glu Glu Asp Gly Glu Asp Leu His Phe
        195                 200                 205 cct acc agt gaa aaa aag ggg att gac cag aat gag caa tgg gtg gtc       730
Pro Thr Ser Glu Lys Lys Gly Ile Asp Gln Asn Glu Gln Trp Val Val
210                 215                 220 ccg caa gtg aag gtg gag aag acc cgc cac acc aga caa gca agc gag       778
Pro Gln Val Lys Val Glu Lys Thr Arg His Thr Arg Gln Ala Ser Glu
225                 230                 235                 240
```

```
gaa gac ctt cct ata aat gac tat act gaa aat gga att gaa ttt gac      826
Glu Asp Leu Pro Ile Asn Asp Tyr Thr Glu Asn Gly Ile Glu Phe Asp
                245                 250                 255 cca atg ctg gat gag aga ggt tac tgt tgt att tac tgt cgt cga ggc      874
Pro Met Leu Asp Glu Arg Gly Tyr Cys Cys Ile Tyr Cys Arg Arg Gly
            260                 265                 270 aac cgt tac tgc cgc cgt gtc tgt gaa cct tta cta ggc tac tac cca      922
Asn Arg Tyr Cys Arg Arg Val Cys Glu Pro Leu Leu Gly Tyr Tyr Pro
            275                 280                 285 tac ccc tac tgc tac caa gga ggt cga gtc atc tgt cgt gtc atc atg      970
Tyr Pro Tyr Cys Tyr Gln Gly Gly Arg Val Ile Cys Arg Val Ile Met
            290                 295                 300 cct tgc aac tgg tgg gtg gcc cgc atg ctt ggg aga gtc taa             1012
Pro Cys Asn Trp Trp Val Ala Arg Met Leu Gly Arg Val
305                 310                 315 taggaagatt gagttcaaac gcttaacctt ctgttagcca atatataatt aatgcatgct    1072
actccatgaa tttctgccta tgaggcattt gcctccaagt agcctatcct tcagaattac   1132
ttgtaggata ttcctctctt catgttctaa taaacttcta catcatca                1180

<210> SEQ ID NO 4
<211> LENGTH: 317
<212> TYPE: PRT
<213> ORGANISM: Mus musculus

<400> SEQUENCE: 4

Met Ala Lys Asn Pro Glu Asn Cys Glu Gly Cys His Ile Leu Asn
1               5                   10                  15

Ala Glu Ala Leu Lys Ser Lys Ile Cys Lys Ser Leu Lys Ile Cys
            20                  25                  30

Gly Leu Val Phe Gly Ile Leu Ala Leu Thr Leu Ile Val Leu Phe Trp
            35                  40                  45

Gly Ser Lys His Phe Trp Pro Glu Val Ser Lys Lys Thr Tyr Asp Met
50                  55                  60

Glu His Thr Phe Tyr Ser Asn Gly Glu Lys Lys Ile Tyr Met Glu
65              70                  75                      80

Ile Asp Pro Ile Thr Arg Thr Glu Ile Phe Arg Ser Gly Asn Gly Thr
                85                  90                  95

Asp Glu Thr Leu Glu Val His Asp Phe Lys Asn Gly Tyr Thr Gly Ile
            100                 105                 110

Tyr Phe Val Gly Leu Gln Lys Cys Phe Ile Lys Thr Gln Ile Lys Val
            115                 120                 125

Ile Pro Glu Phe Ser Glu Pro Glu Glu Ile Asp Glu Asn Glu Glu
            130                 135                 140

Ile Thr Thr Thr Phe Phe Glu Gln Ser Val Ile Trp Val Pro Ala Glu
145                 150                 155                 160

Lys Pro Ile Glu Asn Arg Asp Phe Leu Lys Asn Ser Lys Ile Leu Glu
                165                 170                 175

Ile Cys Asp Asn Val Thr Met Tyr Trp Ile Asn Pro Thr Leu Ile Ala
            180                 185                 190

Val Ser Glu Leu Gln Asp Phe Glu Glu Asp Gly Glu Asp Leu His Phe
            195                 200                 205

Pro Thr Ser Glu Lys Lys Gly Ile Asp Gln Asn Glu Gln Trp Val Val
            210                 215                 220

Pro Gln Val Lys Val Glu Lys Thr Arg His Thr Arg Gln Ala Ser Glu
225                 230                 235                 240
```

```
Glu Asp Leu Pro Ile Asn Asp Tyr Thr Glu Asn Gly Ile Glu Phe Asp
            245                 250                 255

Pro Met Leu Asp Glu Arg Gly Tyr Cys Cys Ile Tyr Cys Arg Arg Gly
            260                 265                 270

Asn Arg Tyr Cys Arg Arg Val Cys Glu Pro Leu Leu Gly Tyr Tyr Pro
            275                 280                 285

Tyr Pro Tyr Cys Tyr Gln Gly Gly Arg Val Ile Cys Arg Val Ile Met
            290                 295                 300

Pro Cys Asn Trp Trp Val Ala Arg Met Leu Gly Arg Val
305                 310                 315

<210> SEQ ID NO 5
<211> LENGTH: 1197
<212> TYPE: DNA
<213> ORGANISM: Rattus norvegicus
<220> FEATURE:
<221> NAME/KEY: CDS
<222> LOCATION: (68)..(1021)
<223> OTHER INFORMATION:

<400> SEQUENCE: 5
actccacctc agcagtggtc tctcagtcct ctcaaagcaa ggaaagagca ctgtgtgctg      60 ggagacc atg gca aag aat cct cca gag aac tgt gag ggc tgt cac att     109
        Met Ala Lys Asn Pro Pro Glu Asn Cys Glu Gly Cys His Ile
         1               5                  10 cta aat gca gaa gct ctg aaa tct aag aag ata cgt aaa tca ctg aag     157
Leu Asn Ala Glu Ala Leu Lys Ser Lys Lys Ile Arg Lys Ser Leu Lys
15              20                  25                  30 att tgt gga cta gtg ttt ggt atc ctg gcc tta act cta att gtc ctg     205
Ile Cys Gly Leu Val Phe Gly Ile Leu Ala Leu Thr Leu Ile Val Leu
                35                  40                  45 ttt tgg ggg agc aaa cac ttc tgg ccc gag gta tcc aag aag acc tat     253
Phe Trp Gly Ser Lys His Phe Trp Pro Glu Val Ser Lys Lys Thr Tyr
            50                  55                  60 ggc atg gag cac act ttc tac agc aat ggc gag aag aag aag att tcc     301
Gly Met Glu His Thr Phe Tyr Ser Asn Gly Glu Lys Lys Lys Ile Ser
        65                  70                  75 atg gaa att gat ccc ata acc aga aca gaa ata ttc aga agt gga aat     349
Met Glu Ile Asp Pro Ile Thr Arg Thr Glu Ile Phe Arg Ser Gly Asn
    80                  85                  90 ggc acc gat gaa aca ttg gaa gtc cat gac ttt aaa aac gga tac act     397
Gly Thr Asp Glu Thr Leu Glu Val His Asp Phe Lys Asn Gly Tyr Thr
95                  100                 105                 110 ggc atc tac ttt gta ggt ctt caa aaa tgc ttt att aaa act caa atc     445
Gly Ile Tyr Phe Val Gly Leu Gln Lys Cys Phe Ile Lys Thr Gln Ile
                115                 120                 125 aaa gtg att cct gaa ttt tct gaa cca gaa gag gaa ata gat gag aat     493
Lys Val Ile Pro Glu Phe Ser Glu Pro Glu Glu Glu Ile Asp Glu Asn
            130                 135                 140 gaa gaa att act aca acg ttc ttt gaa cag tca gtg att tgg gtt cct     541
Glu Glu Ile Thr Thr Thr Phe Phe Glu Gln Ser Val Ile Trp Val Pro
        145                 150                 155 gca gaa aag cct att gaa aac aga gac ttc ctg aaa aat tct aaa att     589
Ala Glu Lys Pro Ile Glu Asn Arg Asp Phe Leu Lys Asn Ser Lys Ile
    160                 165                 170 ctg gag att tgc gac aat gtg act atg tac tgg atc aat ccc act cta     637
Leu Glu Ile Cys Asp Asn Val Thr Met Tyr Trp Ile Asn Pro Thr Leu
175                 180                 185                 190
```

```
ata gca gtt tca gaa tta cag gac ttt gag gag gat ggt gaa gat ctt     685
Ile Ala Val Ser Glu Leu Gln Asp Phe Glu Glu Asp Gly Glu Asp Leu
            195                 200                 205 cac ttt cct acc agc gaa aaa aaa ggg att gac cag aat gag caa tgg     733
His Phe Pro Thr Ser Glu Lys Lys Gly Ile Asp Gln Asn Glu Gln Trp
            210                 215                 220 gtg gtc cca caa gtg aag gtg gag aag acc cgc cgc acc aga caa gca     781
Val Val Pro Gln Val Lys Val Glu Lys Thr Arg Arg Thr Arg Gln Ala
            225                 230                 235 agc gag gaa gac ctt cct gtt aat gac tat act gaa aat gga atc gaa     829
Ser Glu Glu Asp Leu Pro Val Asn Asp Tyr Thr Glu Asn Gly Ile Glu
        240                 245                 250 ttt gat ccc atg ctg gat gag aga ggt tac tgt tgt att tac tgc cgt     877
Phe Asp Pro Met Leu Asp Glu Arg Gly Tyr Cys Cys Ile Tyr Cys Arg
255                 260                 265                 270 cga ggc aac cgc tac tgc cgc agg gtc tgt gaa cct tta cta ggc tac     925
Arg Gly Asn Arg Tyr Cys Arg Arg Val Cys Glu Pro Leu Leu Gly Tyr
                275                 280                 285 tac cca tac ccc tac tgc tac caa gga ggt cga gtc atc tgt cgt gtc     973
Tyr Pro Tyr Pro Tyr Cys Tyr Gln Gly Gly Arg Val Ile Cys Arg Val
            290                 295                 300 atc atg cct tgc aac tgg tgg gtg gcc cgc atg ctt ggg aga gtc taa    1021
Ile Met Pro Cys Asn Trp Trp Val Ala Arg Met Leu Gly Arg Val
            305                 310                 315 taggaagttt gagtccaaat gcttaacctt ttgttagcca acatataatt aatgcatgct  1081
actccatgaa tttctgcatt tgcctccaag tagcctatcc tccagaatta tttgtaggat  1141
attcctctct tcgtgttcta ataaacgtct acatcatcat caaaaaaaaa aaaaaa      1197

<210> SEQ ID NO 6
<211> LENGTH: 317
<212> TYPE: PRT
<213> ORGANISM: Rattus norvegicus

<400> SEQUENCE: 6

Met Ala Lys Asn Pro Pro Glu Asn Cys Glu Gly Cys His Ile Leu Asn
1               5                   10                  15

Ala Glu Ala Leu Lys Ser Lys Lys Ile Arg Lys Ser Leu Lys Ile Cys
            20                  25                  30

Gly Leu Val Phe Gly Ile Leu Ala Leu Thr Leu Ile Val Leu Phe Trp
        35                  40                  45

Gly Ser Lys His Phe Trp Pro Glu Val Ser Lys Thr Tyr Gly Met
    50                  55                  60

Glu His Thr Phe Tyr Ser Asn Gly Glu Lys Lys Lys Ile Ser Met Glu
65                  70                  75                  80

Ile Asp Pro Ile Thr Arg Thr Glu Ile Phe Arg Ser Gly Asn Gly Thr
                85                  90                  95

Asp Glu Thr Leu Glu Val His Asp Phe Lys Asn Gly Tyr Thr Gly Ile
            100                 105                 110

Tyr Phe Val Gly Leu Gln Lys Cys Phe Ile Lys Thr Gln Ile Lys Val
        115                 120                 125

Ile Pro Glu Phe Ser Glu Pro Glu Glu Ile Asp Glu Asn Glu Glu
    130                 135                 140

Ile Thr Thr Thr Phe Phe Glu Gln Ser Val Ile Trp Val Pro Ala Glu
145                 150                 155                 160

Lys Pro Ile Glu Asn Arg Asp Phe Leu Lys Asn Ser Lys Ile Leu Glu
                165                 170                 175
```

```
Ile Cys Asp Asn Val Thr Met Tyr Trp Ile Asn Pro Thr Leu Ile Ala
            180                 185                 190

Val Ser Glu Leu Gln Asp Phe Glu Glu Asp Gly Glu Asp Leu His Phe
        195                 200                 205

Pro Thr Ser Glu Lys Lys Gly Ile Asp Gln Asn Glu Gln Trp Val Val
        210                 215                 220

Pro Gln Val Lys Val Glu Lys Thr Arg Arg Thr Arg Gln Ala Ser Glu
225                 230                 235                 240

Glu Asp Leu Pro Val Asn Asp Tyr Thr Glu Asn Gly Ile Glu Phe Asp
                245                 250                 255

Pro Met Leu Asp Glu Arg Gly Tyr Cys Cys Ile Tyr Cys Arg Arg Gly
            260                 265                 270

Asn Arg Tyr Cys Arg Arg Val Cys Glu Pro Leu Leu Gly Tyr Tyr Pro
            275                 280                 285

Tyr Pro Tyr Cys Tyr Gln Gly Gly Arg Val Ile Cys Arg Val Ile Met
    290                 295                 300

Pro Cys Asn Trp Trp Val Ala Arg Met Leu Gly Arg Val
305                 310                 315

<210> SEQ ID NO 7
<211> LENGTH: 27
<212> TYPE: DNA
<213> ORGANISM: Homo sapiens

<400> SEQUENCE: 7
gagaccatgg caaagaatcc tccagag                                27

<210> SEQ ID NO 8
<211> LENGTH: 24
<212> TYPE: DNA
<213> ORGANISM: Homo sapiens

<400> SEQUENCE: 8
ttagaccctc cccagcatgc gggc                                   24

<210> SEQ ID NO 9
<211> LENGTH: 27
<212> TYPE: DNA
<213> ORGANISM: Mus musculus

<400> SEQUENCE: 9
gagaccatgg caaagaatcc tccagag                                27

<210> SEQ ID NO 10
<211> LENGTH: 24
<212> TYPE: DNA
<213> ORGANISM: Mus musculus

<400> SEQUENCE: 10
ttagactctc ccaagcatgc gggc                                   24

<210> SEQ ID NO 11
<211> LENGTH: 27
<212> TYPE: DNA
<213> ORGANISM: Rattus norvegicus

<400> SEQUENCE: 11
gagaccatgg caaagaatcc tccagag                                27
```

<210> SEQ ID NO 12
<211> LENGTH: 24
<212> TYPE: DNA
<213> ORGANISM: Rattus norvegicus

<400> SEQUENCE: 12
ttagactctc ccaagcatgc gggc                                              24

<210> SEQ ID NO 13
<211> LENGTH: 21
<212> TYPE: DNA
<213> ORGANISM: Homo sapiens

<400> SEQUENCE: 13
gaccctcccc agcatgcggg c                                                 21

<210> SEQ ID NO 14
<211> LENGTH: 21
<212> TYPE: DNA
<213> ORGANISM: Mus musculus

<400> SEQUENCE: 14
gactctccca agcatgcggg c                                                 21

<210> SEQ ID NO 15
<211> LENGTH: 975
<212> TYPE: DNA
<213> ORGANISM: Homo sapiens
<220> FEATURE:
<221> NAME/KEY: CDS
<222> LOCATION: (1)..(975)
<223> OTHER INFORMATION:

<400> SEQUENCE: 15

```
atg gca aag aat cct cca gag aat tgt gaa gac tgt cac att cta aat        48
Met Ala Lys Asn Pro Pro Glu Asn Cys Glu Asp Cys His Ile Leu Asn
1               5                   10                  15 gca gaa gct ttt aaa tcc aag aaa ata tgt aaa tca ctt aag att tgt        96
Ala Glu Ala Phe Lys Ser Lys Lys Ile Cys Lys Ser Leu Lys Ile Cys
            20                  25                  30 gga ctg gtg ttt ggt atc ctg gcc cta act cta att gtc ctg ttt tgg       144
Gly Leu Val Phe Gly Ile Leu Ala Leu Thr Leu Ile Val Leu Phe Trp
        35                  40                  45 ggg agc aag cac ttc tgg ccg gag gta ccc aaa aaa gcc tat gac atg       192
Gly Ser Lys His Phe Trp Pro Glu Val Pro Lys Lys Ala Tyr Asp Met
    50                  55                  60 gag cac act ttc tac agc aat gga gag aag aag aag att tac atg gaa       240
Glu His Thr Phe Tyr Ser Asn Gly Glu Lys Lys Lys Ile Tyr Met Glu
65                  70                  75                  80 att gat cct gtg acc aga act gaa ata ttc aga agc gga aat ggc act       288
Ile Asp Pro Val Thr Arg Thr Glu Ile Phe Arg Ser Gly Asn Gly Thr
                85                  90                  95 gat gaa aca ttg gaa gta cac gac ttt aaa aac gga tac act ggc atc       336
Asp Glu Thr Leu Glu Val His Asp Phe Lys Asn Gly Tyr Thr Gly Ile
            100                 105                 110 tac ttc gtg ggt ctt caa aaa tgt ttt atc aaa act cag att aaa gtg       384
Tyr Phe Val Gly Leu Gln Lys Cys Phe Ile Lys Thr Gln Ile Lys Val
        115                 120                 125 att cct gaa ttt tct gaa cca gaa gag gaa ata gat gag aat gaa gaa       432
Ile Pro Glu Phe Ser Glu Pro Glu Glu Glu Ile Asp Glu Asn Glu Glu
    130                 135                 140
```

| | | |
|---|---|---|
| att acc aca act ttc ttt gaa cag tca gtg att tgg gtc cca gca gaa<br>Ile Thr Thr Thr Phe Phe Glu Gln Ser Val Ile Trp Val Pro Ala Glu<br>145                          150                  155                  160 | 480 |

```
att acc aca act ttc ttt gaa cag tca gtg att tgg gtc cca gca gaa      480
Ile Thr Thr Thr Phe Phe Glu Gln Ser Val Ile Trp Val Pro Ala Glu
145                 150                 155                 160 aag cct att gaa aac cga gat ttt ctt aaa aat tcc aaa att ctg gag      528
Lys Pro Ile Glu Asn Arg Asp Phe Leu Lys Asn Ser Lys Ile Leu Glu
                165                 170                 175 att tgt gat aac gtg acc atg tat tgg atc aat ccc act cta ata tca      576
Ile Cys Asp Asn Val Thr Met Tyr Trp Ile Asn Pro Thr Leu Ile Ser
            180                 185                 190 gtt tct gag tta caa gac ttt gag gag gag gga gaa gat ctt cac ttt      624
Val Ser Glu Leu Gln Asp Phe Glu Glu Glu Gly Glu Asp Leu His Phe
        195                 200                 205 cct gcc aac gaa aaa aaa ggg att gaa caa aat gaa cag tgg gtg gtc      672
Pro Ala Asn Glu Lys Lys Gly Ile Glu Gln Asn Glu Gln Trp Val Val
    210                 215                 220 cct caa gtg aaa gta gag aag acc cgt cac gcc aga caa gca agt gag      720
Pro Gln Val Lys Val Glu Lys Thr Arg His Ala Arg Gln Ala Ser Glu
225                 230                 235                 240 gaa gaa ctt cca ata aat gac tat act gaa aat gga ata gaa ttt gat      768
Glu Glu Leu Pro Ile Asn Asp Tyr Thr Glu Asn Gly Ile Glu Phe Asp
                245                 250                 255 ccc atg ctg gat gag aga ggt tat tgt tgt att tac tgc cgt cga ggc      816
Pro Met Leu Asp Glu Arg Gly Tyr Cys Cys Ile Tyr Cys Arg Arg Gly
            260                 265                 270 aac cgc tat tgc cgc cgc gtc tgt gaa cct tta cta ggc tac tac cca      864
Asn Arg Tyr Cys Arg Arg Val Cys Glu Pro Leu Leu Gly Tyr Tyr Pro
        275                 280                 285 tat cca tac tgc tac caa gga gga cga gtc atc tgt cgt gtc atc atg      912
Tyr Pro Tyr Cys Tyr Gln Gly Gly Arg Val Ile Cys Arg Val Ile Met
    290                 295                 300 cct tgt aac tgg tgg gtg gcc cgc atg ctg ggg agg gtc gct cat cat      960
Pro Cys Asn Trp Trp Val Ala Arg Met Leu Gly Arg Val Ala His His
305                 310                 315                 320 cat cat cat cat taa                                                  975
His His His His
```

<210> SEQ ID NO 16
<211> LENGTH: 324
<212> TYPE: PRT
<213> ORGANISM: Homo sapiens

<400> SEQUENCE: 16

```
Met Ala Lys Asn Pro Pro Glu Asn Cys Glu Asp Cys His Ile Leu Asn
1               5                   10                  15

Ala Glu Ala Phe Lys Ser Lys Ile Cys Lys Ser Leu Lys Ile Cys
            20                  25                  30

Gly Leu Val Phe Gly Ile Leu Ala Leu Thr Leu Ile Val Leu Phe Trp
        35                  40                  45

Gly Ser Lys His Phe Trp Pro Glu Val Pro Lys Ala Tyr Asp Met
    50                  55                  60

Glu His Thr Phe Tyr Ser Asn Gly Glu Lys Lys Ile Tyr Met Glu
65                  70                  75                  80

Ile Asp Pro Val Thr Arg Thr Glu Ile Phe Arg Ser Gly Asn Gly Thr
                85                  90                  95

Asp Glu Thr Leu Glu Val His Asp Phe Lys Asn Gly Tyr Thr Gly Ile
            100                 105                 110

Tyr Phe Val Gly Leu Gln Lys Cys Phe Ile Lys Thr Gln Ile Lys Val
        115                 120                 125
```

```
Ile Pro Glu Phe Ser Glu Pro Glu Glu Ile Asp Glu Asn Glu Glu
    130                 135                 140
Ile Thr Thr Thr Phe Phe Glu Gln Ser Val Ile Trp Val Pro Ala Glu
145                 150                 155                 160
Lys Pro Ile Glu Asn Arg Asp Phe Leu Lys Asn Ser Lys Ile Leu Glu
                165                 170                 175
Ile Cys Asp Asn Val Thr Met Tyr Trp Ile Asn Pro Thr Leu Ile Ser
            180                 185                 190
Val Ser Glu Leu Gln Asp Phe Glu Glu Gly Glu Asp Leu His Phe
        195                 200                 205
Pro Ala Asn Glu Lys Lys Gly Ile Glu Gln Asn Glu Gln Trp Val Val
    210                 215                 220
Pro Gln Val Lys Val Glu Lys Thr Arg His Ala Arg Gln Ala Ser Glu
225                 230                 235                 240
Glu Glu Leu Pro Ile Asn Asp Tyr Thr Glu Asn Gly Ile Glu Phe Asp
                245                 250                 255
Pro Met Leu Asp Glu Arg Gly Tyr Cys Cys Ile Tyr Cys Arg Arg Gly
            260                 265                 270
Asn Arg Tyr Cys Arg Arg Val Cys Glu Pro Leu Leu Gly Tyr Tyr Pro
        275                 280                 285
Tyr Pro Tyr Cys Tyr Gln Gly Gly Arg Val Ile Cys Arg Val Ile Met
    290                 295                 300
Pro Cys Asn Trp Trp Val Ala Arg Met Leu Gly Arg Val Ala His His
305                 310                 315                 320
His His His His
```

<210> SEQ ID NO 17
<211> LENGTH: 975
<212> TYPE: DNA
<213> ORGANISM: Mus musculus
<220> FEATURE:
<221> NAME/KEY: CDS
<222> LOCATION: (1)..(975)
<223> OTHER INFORMATION:

<400> SEQUENCE: 17

```
atg gca aag aat cct cca gag aac tgt gag ggc tgt cac att cta aat      48
Met Ala Lys Asn Pro Pro Glu Asn Cys Glu Gly Cys His Ile Leu Asn
1               5                   10                  15 gca gaa gct ctg aaa tct aag aag ata tgt aaa tca ctg aag att tgt      96
Ala Glu Ala Leu Lys Ser Lys Lys Ile Cys Lys Ser Leu Lys Ile Cys
                20                  25                  30 gga cta gtg ttt ggt atc ctg gcc tta act cta att gtc ctg ttt tgg     144
Gly Leu Val Phe Gly Ile Leu Ala Leu Thr Leu Ile Val Leu Phe Trp
            35                  40                  45 ggg agc aaa cac ttc tgg ccc gag gta tcc aag aaa acc tat gac atg     192
Gly Ser Lys His Phe Trp Pro Glu Val Ser Lys Lys Thr Tyr Asp Met
        50                  55                  60 gag cac act ttc tac agc aac ggc gag aag aag aag att tac atg gaa     240
Glu His Thr Phe Tyr Ser Asn Gly Glu Lys Lys Lys Ile Tyr Met Glu
65                  70                  75                  80 att gat ccc ata acc aga aca gaa ata ttc aga agt gga aat ggc act     288
Ile Asp Pro Ile Thr Arg Thr Glu Ile Phe Arg Ser Gly Asn Gly Thr
                85                  90                  95 gat gaa aca ttg gaa gtc cat gac ttt aaa aat gga tac act ggc atc     336
Asp Glu Thr Leu Glu Val His Asp Phe Lys Asn Gly Tyr Thr Gly Ile
                100                 105                 110
```

|  |  |
|---|---|
| tac ttt gta ggt ctt caa aaa tgc ttt att aaa act caa atc aaa gtg<br>Tyr Phe Val Gly Leu Gln Lys Cys Phe Ile Lys Thr Gln Ile Lys Val<br>        115                   120                  125 | 384 |
| att cct gaa ttt tct gaa cca gag gaa gaa ata gat gag aat gaa gaa<br>Ile Pro Glu Phe Ser Glu Pro Glu Glu Glu Ile Asp Glu Asn Glu Glu<br>130                   135                   140 | 432 |
| att act aca act ttc ttt gaa cag tca gtg att tgg gtt ccc gca gaa<br>Ile Thr Thr Thr Phe Phe Glu Gln Ser Val Ile Trp Val Pro Ala Glu<br>145                   150                   155                  160 | 480 |
| aag cct att gaa aac aga gac ttc ctg aaa aat tct aaa att ctg gag<br>Lys Pro Ile Glu Asn Arg Asp Phe Leu Lys Asn Ser Lys Ile Leu Glu<br>                   165                   170                   175 | 528 |
| att tgc gat aat gtg acc atg tac tgg atc aat ccc act cta ata gca<br>Ile Cys Asp Asn Val Thr Met Tyr Trp Ile Asn Pro Thr Leu Ile Ala<br>                   180                   185                   190 | 576 |
| gtt tca gaa tta cag gac ttt gag gag gac ggt gaa gat ctt cac ttt<br>Val Ser Glu Leu Gln Asp Phe Glu Glu Asp Gly Glu Asp Leu His Phe<br>                   195                   200                   205 | 624 |
| cct acc agt gaa aaa aag ggg att gac cag aat gag caa tgg gtg gtc<br>Pro Thr Ser Glu Lys Lys Gly Ile Asp Gln Asn Glu Gln Trp Val Val<br>        210                   215                   220 | 672 |
| ccg caa gtg aag gtg gag aag acc cgc cac acc aga caa gca agc gag<br>Pro Gln Val Lys Val Glu Lys Thr Arg His Thr Arg Gln Ala Ser Glu<br>225                   230                   235                  240 | 720 |
| gaa gac ctt cct ata aat gac tat act gaa aat gga att gaa ttt gac<br>Glu Asp Leu Pro Ile Asn Asp Tyr Thr Glu Asn Gly Ile Glu Phe Asp<br>                   245                   250                   255 | 768 |
| cca atg ctg gat gag aga ggt tac tgt tgt att tac tgt cgt cga ggc<br>Pro Met Leu Asp Glu Arg Gly Tyr Cys Cys Ile Tyr Cys Arg Arg Gly<br>                   260                   265                   270 | 816 |
| aac cgt tac tgc cgc cgt gtc tgt gaa cct tta cta ggc tac tac cca<br>Asn Arg Tyr Cys Arg Arg Val Cys Glu Pro Leu Leu Gly Tyr Tyr Pro<br>                   275                   280                   285 | 864 |
| tac ccc tac tgc tac caa gga ggt cga gtc atc tgt cgt gtc atc atg<br>Tyr Pro Tyr Cys Tyr Gln Gly Gly Arg Val Ile Cys Arg Val Ile Met<br>        290                   295                   300 | 912 |
| cct tgc aac tgg tgg gtg gcc cgc atg ctt ggg aga gtc gct cat cat<br>Pro Cys Asn Trp Trp Val Ala Arg Met Leu Gly Arg Val Ala His His<br>305                   310                   315                  320 | 960 |
| cat cat cat cat taa<br>His His His His | 975 |

<210> SEQ ID NO 18
<211> LENGTH: 324
<212> TYPE: PRT
<213> ORGANISM: Mus musculus

<400> SEQUENCE: 18

Met Ala Lys Asn Pro Pro Glu Asn Cys Glu Gly Cys His Ile Leu Asn
1               5                   10                  15

Ala Glu Ala Leu Lys Ser Lys Lys Ile Cys Lys Ser Leu Lys Ile Cys
            20                  25                  30

Gly Leu Val Phe Gly Ile Leu Ala Leu Thr Leu Ile Val Leu Phe Trp
        35                  40                  45

Gly Ser Lys His Phe Trp Pro Glu Val Ser Lys Lys Thr Tyr Asp Met
    50                  55                  60

Glu His Thr Phe Tyr Ser Asn Gly Glu Lys Lys Lys Ile Tyr Met Glu
65                  70                  75                  80

```
Ile Asp Pro Ile Thr Arg Thr Glu Ile Phe Arg Ser Gly Asn Gly Thr
                85                  90                  95

Asp Glu Thr Leu Glu Val His Asp Phe Lys Asn Gly Tyr Thr Gly Ile
            100                 105                 110

Tyr Phe Val Gly Leu Gln Lys Cys Phe Ile Lys Thr Gln Ile Lys Val
        115                 120                 125

Ile Pro Glu Phe Ser Glu Pro Glu Glu Ile Asp Glu Asn Glu Glu
    130                 135                 140

Ile Thr Thr Thr Phe Phe Glu Gln Ser Val Ile Trp Val Pro Ala Glu
145                 150                 155                 160

Lys Pro Ile Glu Asn Arg Asp Phe Leu Lys Asn Ser Lys Ile Leu Glu
                165                 170                 175

Ile Cys Asp Asn Val Thr Met Tyr Trp Ile Asn Pro Thr Leu Ile Ala
                180                 185                 190

Val Ser Glu Leu Gln Asp Phe Glu Glu Asp Gly Glu Asp Leu His Phe
            195                 200                 205

Pro Thr Ser Glu Lys Lys Gly Ile Asp Gln Asn Glu Gln Trp Val Val
        210                 215                 220

Pro Gln Val Lys Val Lys Thr Arg His Thr Arg Gln Ala Ser Glu
225                 230                 235                 240

Glu Asp Leu Pro Ile Asn Asp Tyr Thr Glu Asn Gly Ile Glu Phe Asp
                245                 250                 255

Pro Met Leu Asp Glu Arg Gly Tyr Cys Cys Ile Tyr Cys Arg Arg Gly
            260                 265                 270

Asn Arg Tyr Cys Arg Arg Val Cys Glu Pro Leu Leu Gly Tyr Tyr Pro
        275                 280                 285

Tyr Pro Tyr Cys Tyr Gln Gly Gly Arg Val Ile Cys Arg Val Ile Met
    290                 295                 300

Pro Cys Asn Trp Trp Val Ala Arg Met Leu Gly Arg Val Ala His His
305                 310                 315                 320

His His His His

<210> SEQ ID NO 19
<211> LENGTH: 69
<212> TYPE: DNA
<213> ORGANISM: Artificial Sequence
<220> FEATURE:
<223> OTHER INFORMATION: signal sequence of preprotrypsin and FLAG
      peptide
<220> FEATURE:
<221> NAME/KEY: CDS
<222> LOCATION: (1)..(69)
<223> OTHER INFORMATION:

<400> SEQUENCE: 19 atg tct gca ctt ctg atc cta gct ctt gtt gga gct gca gtt gct gac      48
Met Ser Ala Leu Leu Ile Leu Ala Leu Val Gly Ala Ala Val Ala Asp
1               5                   10                  15 tac aaa gac gat gac gac aag                                          69
Tyr Lys Asp Asp Asp Asp Lys
            20

<210> SEQ ID NO 20
<211> LENGTH: 23
<212> TYPE: PRT
<213> ORGANISM: Artificial Sequence
<220> FEATURE:
<223> OTHER INFORMATION: signal sequence of preprotrypsin and FLAG
      peptide
```

-continued

```
<400> SEQUENCE: 20

Met Ser Ala Leu Leu Ile Leu Ala Leu Val Gly Ala Ala Val Ala Asp
1               5                   10                  15

Tyr Lys Asp Asp Asp Asp Lys
            20

<210> SEQ ID NO 21
<211> LENGTH: 23
<212> TYPE: DNA
<213> ORGANISM: Homo sapiens

<400> SEQUENCE: 21
gagggagaag atcttcactt tcc                                                   23

<210> SEQ ID NO 22
<211> LENGTH: 432
<212> TYPE: DNA
<213> ORGANISM: Artificial Sequence
<220> FEATURE:
<223> OTHER INFORMATION: signal sequence of preprotrypsin, FLAG peptide
      and C terminal region of ChM1L
<220> FEATURE:
<221> NAME/KEY: CDS
<222> LOCATION: (1)..(432)
<223> OTHER INFORMATION:

<400> SEQUENCE: 22 atg tct gca ctt ctg atc cta gct ctt gtt gga gct gca gtt gct gac    48
Met Ser Ala Leu Leu Ile Leu Ala Leu Val Gly Ala Ala Val Ala Asp
1               5                   10                  15 tac aaa gac gat gac gac aag ctg gaa ttc gat gag gga gaa gat ctt    96
Tyr Lys Asp Asp Asp Asp Lys Leu Glu Phe Asp Glu Gly Glu Asp Leu
            20                  25                  30 cac ttt cct gcc aac gaa aaa aaa ggg att gaa caa aat gaa cag tgg   144
His Phe Pro Ala Asn Glu Lys Lys Gly Ile Glu Gln Asn Glu Gln Trp
        35                  40                  45 gtg gtc cct caa gtg aaa gta gag aag acc cgt cac gcc aga caa gca   192
Val Val Pro Gln Val Lys Val Glu Lys Thr Arg His Ala Arg Gln Ala
    50                  55                  60 agt gag gaa gaa ctt cca ata aat gac tat act gaa aat gga ata gaa   240
Ser Glu Glu Glu Leu Pro Ile Asn Asp Tyr Thr Glu Asn Gly Ile Glu
65                  70                  75                  80 ttt gat ccc atg ctg gat gag aga ggt tat tgt tgt att tac tgc cgt   288
Phe Asp Pro Met Leu Asp Glu Arg Gly Tyr Cys Cys Ile Tyr Cys Arg
                85                  90                  95 cga ggc aac cgc tat tgc cgc gcc gtc tgt gaa cct tta cta ggc tac   336
Arg Gly Asn Arg Tyr Cys Arg Ala Val Cys Glu Pro Leu Leu Gly Tyr
            100                 105                 110 tac cca tat cca tac tgc tac caa gga gga cga gtc atc tgt cgt gtc   384
Tyr Pro Tyr Pro Tyr Cys Tyr Gln Gly Gly Arg Val Ile Cys Arg Val
        115                 120                 125 atc atg cct tgt aac tgg tgg gtg gcc cgc atg ctg ggg agg gtc taa   432
Ile Met Pro Cys Asn Trp Trp Val Ala Arg Met Leu Gly Arg Val
    130                 135                 140

<210> SEQ ID NO 23
<211> LENGTH: 143
<212> TYPE: PRT
<213> ORGANISM: Artificial Sequence
<220> FEATURE:
<223> OTHER INFORMATION: signal sequence of preprotrypsin, FLAG peptide
      and C terminal region of ChM1L
```

```
<400> SEQUENCE: 23

Met Ser Ala Leu Leu Ile Leu Ala Leu Val Gly Ala Ala Val Ala Asp
1               5                   10                  15

Tyr Lys Asp Asp Asp Asp Lys Leu Glu Phe Asp Glu Gly Glu Asp Leu
            20                  25                  30

His Phe Pro Ala Asn Glu Lys Lys Gly Ile Glu Gln Asn Glu Gln Trp
            35                  40                  45

Val Val Pro Gln Val Lys Val Glu Lys Thr Arg His Ala Arg Gln Ala
    50                  55                  60

Ser Glu Glu Glu Leu Pro Ile Asn Asp Tyr Thr Glu Asn Gly Ile Glu
65                  70                  75                  80

Phe Asp Pro Met Leu Asp Glu Arg Gly Tyr Cys Cys Ile Tyr Cys Arg
                85                  90                  95

Arg Gly Asn Arg Tyr Cys Arg Arg Val Cys Glu Pro Leu Leu Gly Tyr
                100                 105                 110

Tyr Pro Tyr Pro Tyr Cys Tyr Gln Gly Gly Arg Val Ile Cys Arg Val
                115                 120                 125

Ile Met Pro Cys Asn Trp Trp Val Ala Arg Met Leu Gly Arg Val
            130                 135                 140

<210> SEQ ID NO 24
<211> LENGTH: 21
<212> TYPE: DNA
<213> ORGANISM: Mus musculus

<400> SEQUENCE: 24
tcagccatga cagagaactc a                                          21

<210> SEQ ID NO 25
<211> LENGTH: 21
<212> TYPE: DNA
<213> ORGANISM: Mus musculus

<400> SEQUENCE: 25
ttacaccatg cccaagatgc g                                          21
```